United States Patent
Sun et al.

(10) Patent No.: US 10,920,268 B2
(45) Date of Patent: Feb. 16, 2021

(54) METHODS AND COMPOSITIONS FOR ISOLATING ASYMMETRIC NUCLEIC ACID COMPLEXES

(71) Applicant: Pacific Biosciences of California, Inc., Menlo Park, CA (US)

(72) Inventors: Lei Sun, San Jose, CA (US); Sassan Sheikholeslami, San Francisco, CA (US); Natasha Popovich, Belmont, CA (US); David Christopher Scherer, Palo Alto, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 283 days.

(21) Appl. No.: 16/036,511

(22) Filed: Jul. 16, 2018

(65) Prior Publication Data
US 2019/0024140 A1 Jan. 24, 2019

Related U.S. Application Data

(60) Provisional application No. 62/534,065, filed on Jul. 18, 2017.

(51) Int. Cl.
*C12Q 1/6806* (2018.01)
(52) U.S. Cl.
CPC ............................ *C12Q 1/6806* (2013.01)
(58) Field of Classification Search
CPC ... C12Q 1/6806; C12Q 1/6855; C12Q 1/6869
See application file for complete search history.

(56) References Cited

U.S. PATENT DOCUMENTS

| | | | |
|---|---|---|---|
| 6,787,310 B2 | 9/2004 | Chiesa et al. |
| 7,635,566 B2 | 12/2009 | Brenner |
| 8,143,030 B2 | 3/2012 | Maxham et al. |
| 8,153,375 B2 | 4/2012 | Travers et al. |
| 8,241,850 B2 | 8/2012 | Brenner |
| 8,658,364 B2 | 2/2014 | Pham et al. |
| 8,715,930 B2 | 5/2014 | Pham et al. |
| 8,936,911 B2 | 1/2015 | Sun et al. |
| 9,267,168 B2 | 2/2016 | Miller et al. |
| 9,416,409 B2 | 8/2016 | Hayden |
| 2007/0128624 A1 | 6/2007 | Gormley et al. |
| 2012/0071359 A1 | 3/2012 | Sun et al. |
| 2012/0122161 A1 | 5/2012 | Musgrave-Brown et al. |

(Continued)

FOREIGN PATENT DOCUMENTS

| | | | |
|---|---|---|---|
| WO | 2016059363 A1 | 4/2016 | |
| WO | WO-2018015365 A1 * | 1/2018 | ........... C12Q 1/6869 |

OTHER PUBLICATIONS

International Search Report and Written Opinion dated Nov. 29, 2018 for related PCT/US2018/042306.

(Continued)

*Primary Examiner* — Angela M. Bertagna
(74) *Attorney, Agent, or Firm* — Monicia Elrod-Erickson

(57) ABSTRACT

The present disclosure provides improved methods for isolating asymmetrically-primed and/or asymmetrically-tagged nucleic acid complexes that find use in downstream analytical analyses, including sequence analysis. Compositions comprising such complexes and kits and systems for generating such complexes are also provided.

19 Claims, 12 Drawing Sheets

(56) References Cited

U.S. PATENT DOCUMENTS

| | | | |
|---|---|---|---|
| 2012/0322666 A1* | 12/2012 | Pham | G01N 33/54313 |
| | | | 506/2 |
| 2013/0330722 A1* | 12/2013 | Miller | C12N 15/1003 |
| | | | 435/6.11 |
| 2014/0134610 A1 | 5/2014 | Pham et al. | |
| 2016/0208241 A1 | 1/2016 | Tsai et al. | |
| 2017/0362639 A1 | 12/2017 | Wilson | |
| 2018/0340157 A1 | 11/2018 | Franklin et al. | |

OTHER PUBLICATIONS

International Preliminary Report on Patentability dated Jan. 30, 2020 for related PCT/US2018/042306.

* cited by examiner

Lane 1: Symmetric template before extension
Lane 2: Symmetric template after extension
Lane 3: Mix-primer oligo-hook template before extension
Lane 4: Mix-primer oligo-hook template after extension

Symmetrically-primed

| Mapping Report | |
|---|---|
| Value | Analysis Metric (Mapped) |
| 86.13% | Mean concordance |
| 625,274 | Number of Subreads |
| 1,647,802,319 | Number of Subread Bases |
| 2,635 | Subread Length Mean |
| 3,884 | Subread Length N50 |
| 4,520 | Subread Length 95% |
| 12,919 | Subread Length Max |
| 311,264 | Number of Polymerase Reads |
| 5,373 | Polymerase Read Length Mean |
| 12,174 | Polymerase Read N50 |
| 19,630 | Polymerase Read Length 95% |
| 29,273 | Polymerase Read Length Max |

Asymmetrically-primed

| Mapping Report | |
|---|---|
| Value | Analysis Metric (Mapped) |
| 87.22% | Mean concordance |
| 160,951 | Number of Subreads |
| 519,069,258 | Number of Subread Bases |
| 3,225 | Subread Length Mean |
| 4,215 | Subread Length N50 |
| 4,550 | Subread Length 95% |
| 19,607 | Subread Length Max |
| 48,993 | Number of Polymerase Reads |
| 11,098 | Polymerase Read Length Mean |
| 21,450 | Polymerase Read N50 |
| 30,610 | Polymerase Read Length 95% |
| 41,580 | Polymerase Read Length Max |

LS_4kAsy_Blasso_MBS_4hr

| Mapping Report | |
|---|---|
| Value | Analysis Metric (Mapped) |
| 86.99% | Mean concordance |
| 950,999 | Number of Subreads |
| 3,064,194,637 | Number of Subread Bases |
| 3,222 | Subread Length Mean |
| 4,339 | Subread Length N50 |
| 4,580 | Subread Length 95% |
| 17,991 | Subread Length Max |
| 315,372 | Number of Polymerase Reads |
| 9,862 | Polymerase Read Length Mean |
| 16,038 | Polymerase Read N50 |
| 21,410 | Polymerase Read Length 95% |
| 28,564 | Polymerase Read Length Max |

LS_4kAsy_Blasso_Dif_4hr

| Mapping Report | |
|---|---|
| Value | Analysis Metric (Mapped) |
| 87.45% | Mean concordance |
| 1,211,665 | Number of Subreads |
| 3,886,423,193 | Number of Subread Bases |
| 3,208 | Subread Length Mean |
| 4,336 | Subread Length N50 |
| 4,560 | Subread Length 95% |
| 15,157 | Subread Length Max |
| 391,079 | Number of Polymerase Reads |
| 10,084 | Polymerase Read Length Mean |
| 16,311 | Polymerase Read N50 |
| 21,520 | Polymerase Read Length 95% |
| 28,965 | Polymerase Read Length Max |

METHODS AND COMPOSITIONS FOR ISOLATING ASYMMETRIC NUCLEIC ACID COMPLEXES

CROSS-REFERENCE TO RELATED APPLICATIONS

This application claims the benefit of priority to U.S. Provisional Patent Application 62/534,065 filed Jul. 18, 2017, entitled "Methods and Compositions for Isolating Asymmetric Nucleic Acid Complexes", which is hereby incorporated by reference herein in its entirety.

BACKGROUND OF THE INVENTION

The ability to understand the genetic code that serves as the blueprint for the framework of all life has yielded countless advances in countless areas. From the ability to diagnose disease to the ability to identify evolutionary connections and/or diversity, to the ability to manipulate the genetic framework in the development of new materials and compositions, this understanding has opened doors to innumerable advances that have benefitted and will continue to benefit the human race.

Integral to these advances have been the advances in technology directed to the reading and/or characterization of the genetic code. For example, development of nucleic acid sequencing technologies has allowed for the base by base identification of the nucleic acid sequences that make up the genetic code to the point that entire human genomes have been elucidated. Other advances include rapid array based technologies that allow reasonably facile identification of genetic patterns from patients or other biological samples.

With each technological advance, there exist opportunities to further improve the state of the art through advances in related or ancillary technologies associated with those advanced areas. For example, advances in fluorescent dye chemistries have fueled many advances in genetic technologies by permitting simple optical analyses of biological reactions and their products. Likewise, development of microfluidic technologies have provided for advances in fluid and reagent handling to yield a reproducibility that had not been previously achievable through more conventional means.

As detailed below, the present disclosure provides improved methods for isolating specific nucleic acid complexes that find use in numerous downstream analyses, including single molecule sequence analysis.

BRIEF SUMMARY OF THE INVENTION

The present disclosure provides improved methods for isolating asymmetrically-primed and/or asymmetrically-tagged nucleic acid complexes that find use in downstream analytical analyses, including sequence analysis. Compositions comprising such complexes and kits and systems for generating such complexes are also provided.

Aspects of the present disclosure include a method for isolating asymmetrically-primed nucleic acid templates comprising: obtaining a sample comprising a mixture of symmetrically-primed nucleic acid templates and asymmetrically-primed nucleic acid templates, wherein the nucleic acid templates comprise a double-stranded insert region with hairpin adapters at both ends, wherein each symmetrically-primed nucleic acid template comprises capture primers hybridized to both terminal hairpin adapters or synthesis primers hybridized to both terminal hairpin adapters, and wherein each asymmetrically-primed nucleic acid template comprises a capture primer hybridized to the hairpin adapter at one end and a synthesis primer hybridized to the hairpin adapter at the opposite end; contacting the sample to a solid support comprising an immobilized binding moiety specific for a capture region on the capture primer, thereby immobilizing capture primer-hybridized nucleic acid templates to the solid support; contacting the nucleic acid templates immobilized to the solid support with a nucleic acid polymerase having strand displacement activity under conditions that promote nucleic acid synthesis from the synthesis primer; and collecting nucleic acid templates eluted from the solid support-immobilized capture primers by the strand displacement activity of the nucleic acid polymerase, thereby isolating asymmetrically-primed nucleic acid templates.

In certain embodiments, the asymmetrically-primed nucleic acid templates are symmetrically-tagged with a first hairpin adapter comprising a primer binding site, wherein the capture primer and the synthesis primer are specific for the primer binding site, and wherein the capture primer and the synthesis primer cannot bind to the same primer binding site simultaneously.

In certain embodiments, the sample is obtained by contacting symmetrically-tagged nucleic acid templates with the capture primer and the synthesis primer under nucleic acid hybridization conditions.

In certain embodiments, the capture primer and the synthesis primer are at a molar ratio of 1:1.

In certain embodiments, the symmetrically-primed nucleic acid templates are symmetrically-tagged with either a first hairpin adapter or a second hairpin adapter and the asymmetrically-primed nucleic acid templates are asymmetrically tagged with the first hairpin adapter at one end and the second hairpin adapter at the opposite end, wherein the first hairpin adapter comprises a synthesis primer binding site specific for the synthesis primer and the second hairpin adapter comprises a capture primer binding site specific for the capture primer.

In certain embodiments, the sample is obtained by annealing the capture primer and the synthesis primer to a mixture of the symmetrically-tagged and the asymmetrically tagged nucleic acid templates.

In certain embodiments, nucleic acid synthesis is allowed to continue after elution of the nucleic acid templates from the solid support.

In certain embodiments, the capture region on the capture primer is a binding partner for the immobilized binding moiety on the solid support.

In certain embodiments, the binding partner is selected from the group consisting of: a nucleotide sequence, an antigen, an antibody or a binding fragment thereof, avidin, streptavidin, and biotin.

Aspects of the present disclosure include a method for isolating nucleic acid synthesis-competent nucleic acid templates comprising: obtaining a sample comprising asymmetrically-tagged nucleic acid templates each comprising a double-stranded insert region, a first hairpin adapter at one end, and a second hairpin adapter at the opposite end, wherein the first hairpin adapter comprises a synthesis primer binding site and a capture primer binding site positioned 3' of the synthesis primer binding site; contacting the nucleic acid sample with a capture primer specific for the capture primer binding site under nucleic acid hybridization conditions; immobilizing capture primer-hybridized nucleic acid templates to a solid support via a capture region on the capture primer; contacting the nucleic acid templates immobilized to the solid support with a nucleic acid polymerase having strand displacement activity under conditions that promote nucleic acid synthesis from a synthesis primer hybridized to the synthesis primer binding site; and collecting nucleic acid templates eluted from the solid support by the strand displacement activity of the nucleic acid polymerase, thereby isolating nucleic acid synthesis competent nucleic acid templates.

In certain embodiments, the synthesis primer is contacted to the sample with the capture primer in the first contacting step.

In certain embodiments, the synthesis primer is contacted to the sample under nucleic acid hybridization conditions after the immobilizing step.

In certain embodiments, the capture primer is covalently bound to the solid support via the capture region.

In certain embodiments, the capture primer is non-covalently bound to the solid support via the capture region.

In certain embodiments, the solid support comprises a binding partner for the capture region on the capture primer.

In certain embodiments, the binding partner is selected from the group consisting of: a nucleotide sequence, an antigen, an antibody or a binding fragment thereof, avidin, streptavidin, and biotin.

In certain embodiments, the sample further comprises symmetrically-tagged nucleic acid templates each comprising either the first hairpin adapter at both ends or the second hairpin adapter at both ends, wherein the second hairpin adapter comprises a second capture primer binding site, wherein before the first contacting step, the method further comprises: contacting the nucleic acid sample with a second capture primer specific for the second capture primer binding site under nucleic acid hybridization conditions; immobilizing second capture primer-hybridized nucleic acid templates to a second solid support via a capture region on the second capture primer; and eluting and collecting the nucleic acid templates bound to the second solid support.

In certain embodiments, the second capture primer is covalently bound to the second solid support via the capture region on the second capture primer.

In certain embodiments, the second capture primer is non-covalently bound to the second solid support via the capture region on the second capture primer.

In certain embodiments, the second solid support comprises a binding partner for the capture region on the second capture primer.

In certain embodiments, the binding partner is selected from the group consisting of: a nucleotide sequence, an antigen, an antibody or a binding fragment thereof, avidin, streptavidin, and biotin.

In certain embodiments, eluting from the second solid substrate is not achieved by strand displacement nucleic acid synthesis.

In certain embodiments, the strand displacing polymerase is a Φ29 DNA polymerase, a homolog of a Φ29 DNA polymerase, a modified version of a Φ29 DNA polymerase, or a modified version of a homolog of a Φ29 DNA polymerase.

In certain embodiments, the isolated nucleic acid templates are subjected to sequence analysis.

In certain embodiments, the sequence analysis comprises a sequencing-by-synthesis sequencing reaction.

In certain embodiments, the nucleic acid polymerase associated with the template nucleic acids after elution is used in the sequencing-by-synthesis sequencing reaction.

In certain embodiments, the sequencing reaction is a single molecule, real-time sequencing reaction.

In certain embodiments, the sequence analysis comprises a nanopore-based sequencing reaction.

Aspects of the present disclosure include a kit comprising: a first hairpin adapter comprising a primer binding site; a capture primer specific for the primer binding site; and a synthesis primer specific for the primer binding site; wherein the capture primer and the synthesis primer cannot bind to the same primer binding site simultaneously.

Aspects of the present disclosure include a kit comprising: a first hairpin adapter comprising a synthesis primer binding site and a capture primer binding site, wherein the capture primer binding site is positioned 3' of the synthesis primer binding site; a second hairpin adapter; a capture primer specific for the capture primer binding site; and a synthesis primer specific for the synthesis primer binding site.

In certain embodiments, the kit(s) further comprise a solid substrate comprising immobilized binding partners specific for a capture region on the capture primer.

In certain embodiments, the capture primer is covalently attached to a solid substrate.

Aspects of the present disclosure include a kit comprising: a first hairpin adapter comprising a synthesis primer binding site and a first capture primer binding site, wherein the first capture primer binding site is positioned 3' of the synthesis primer binding site; a second hairpin adapter comprising a second capture primer binding site; a first capture primer specific for the first capture primer binding site; a second capture primer specific for the second capture primer binding site; and a synthesis primer specific for the synthesis primer binding site.

In certain embodiments, the kit further comprises: a first solid substrate comprising immobilized binding partners specific for a first capture region on the first capture primer; and a second solid substrate comprising immobilized binding partners specific for a second capture region on the second capture primer.

In certain embodiments, the first capture primer is covalently attached to a first solid substrate.

In certain embodiments, the second capture primer is covalently attached to a second solid substrate.

In certain embodiments, the kit further comprises a strand displacing polymerase enzyme.

In certain embodiments, the strand displacing polymerase enzyme is a Φ29 DNA polymerase, a homolog of a Φ29 DNA polymerase, a modified version of a Φ29 DNA polymerase, or a modified version of a homolog of a Φ29 DNA polymerase.

In certain embodiments, the kit further comprises one or more reagents and/or buffers for performing a nucleic acid synthesis reaction.

In certain embodiments, the kit further comprises one or more reagents and/or buffers for attaching hairpin adapters to linear double-stranded nucleic acids.

In certain embodiments, the kit further comprises one or more component for nucleic acid isolation, nucleic acid enrichment, and/or nucleic acid size selection.

DETAILED DESCRIPTION OF THE INVENTION

Figure 1:
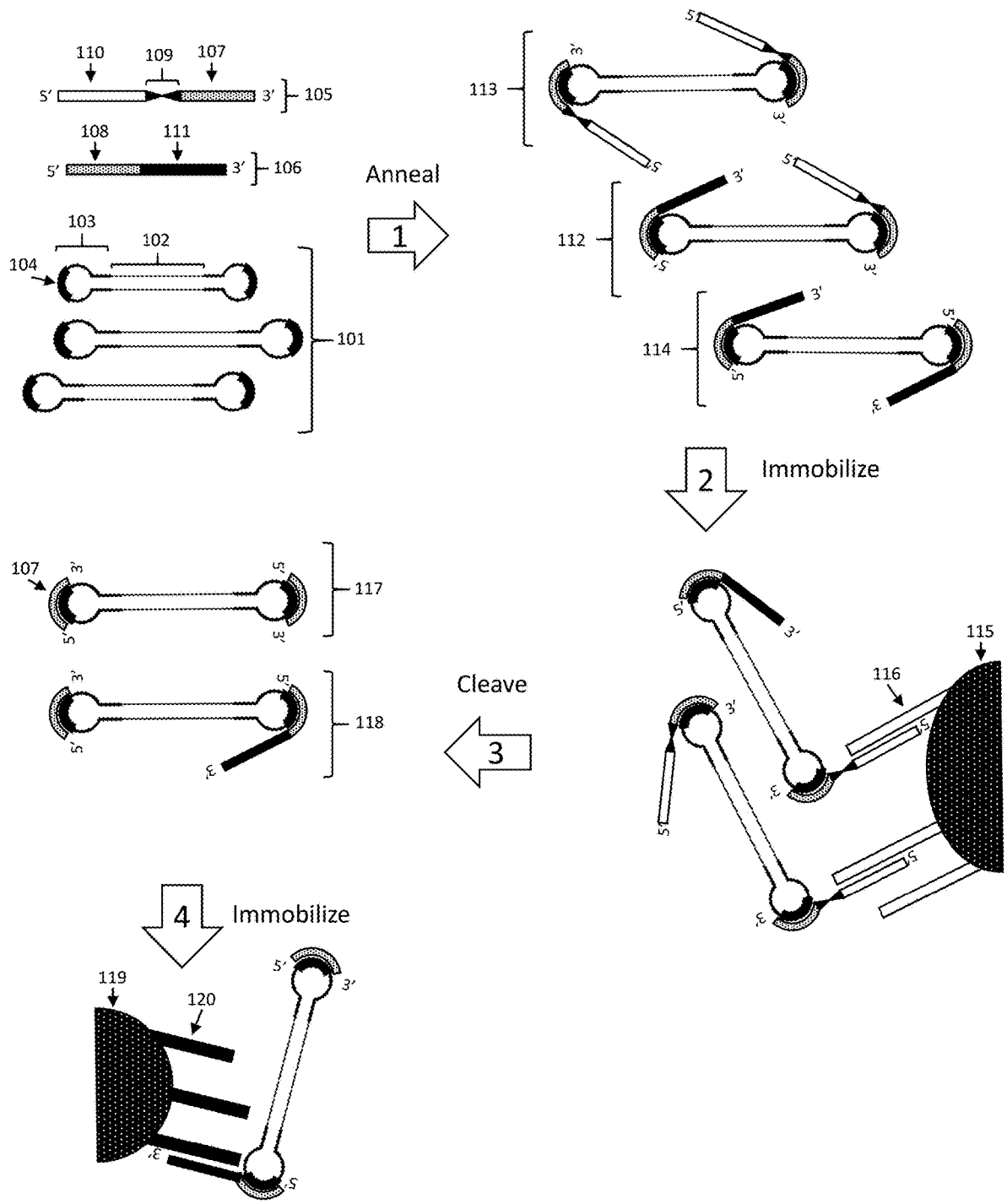
FIG. 1 illustrates an embodiment of a workflow for isolating asymmetrically-primed nucleic acids from a nucleic acid sample comprising symmetrically-tagged nucleic acid templates that employs a synthesis primer cleavably-linked to a capture region.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, *IRL Press, London*, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

By "nucleic acid", "polynucleotide", "oligonucleotide", or grammatical equivalents herein means at least two nucleotides covalently linked together. A nucleic acid of the present invention will generally contain phosphodiester bonds, although in some cases, nucleic acid analogs are included that may have alternate backbones, comprising, for example, phosphoramide, phosphorothioate, phosphorodithioate, and peptide nucleic acid (PNA) backbones and linkages. Other analog nucleic acids include those with positive backbones; non-ionic backbones, and non-ribose backbones, including those described in U.S. Pat. No. 5,235,033 (titled "Alpha-morpholino ribonucleoside derivatives and polymers thereof") and U.S. Pat. No. 5,034,506 (titled "Uncharged morpholino-based polymers having achiral intersubunit linkages"). The template nucleic acid may also have other modifications, such as the inclusion of heteroatoms, the attachment of labels, such as dyes, or substitution with functional groups which will still allow for base pairing and for recognition by the enzyme.

Oligonucleotides employed in the present disclosure that are designed to anneal specifically to a sufficiently complementary nucleic acid sequence in a target nucleic acid under appropriately stringent hybridization conditions are sometimes referred to herein as "primers", while the sequence to which they anneal is referred to as the "primer binding site". Thus, a primer that is "specific for" a primer binding site in a nucleic acid, e.g., a primer binding site in an adapter, is one that includes a nucleic acid sequence that hybridizes preferentially to the primer binding site under appropriately stringent hybridizations conditions. Appropriately stringent hybridization conditions are regularly determined by the ordinarily skilled person in the art. The nucleic acid sequence in a primer that hybridizes to the primer binding site is sometimes referred to herein as the "primer region" or similar phrase. Primers often include regions that do not participate directly in hybridizing to the primer binding site which may have a particular use in methods described herein. Primers can be used for different functions, including but not limited to nucleic acid synthesis and/or capture of nucleic acids containing their cognate primer binding site. For example, a "capture primer" (or "capture oligonucleotide") can be used to isolate nucleic acids that contain the specific capture primer binding site, e.g., present in an adapter sequence, and often include a first member of a binding pair (e.g., a nucleic acid sequence, biotin, avidin, antigen, antibody or binding fragment thereof, etc.) or are attached directly to a solid support. As another example, a "synthesis primer" is one that can be used to prime nucleic acid synthesis by a nucleic acid polymerase (under nucleic acid synthesis conditions) and, in certain specific applications, can be used as a sequencing primer in sequencing-by-synthesis (SBS) applications.

As used herein, a "substantially identical" nucleic acid is one that has at least 80%, 85%, 90%, 95%, 96%, 97%, 98% or 99% sequence identity to a reference nucleic acid sequence. The length of comparison is preferably the full length of the nucleic acid, but is generally at least 20 nucleotides, 30 nucleotides, 40 nucleotides, 50 nucleotides, 75 nucleotides, 100 nucleotides, 125 nucleotides, or more.

By "asymmetric nucleic acid" is meant a nucleic acid that has a different nucleic acid composition at the first end of the nucleic acid as compared to the second end of the nucleic acid. In certain embodiments, the nucleic acid composition at the first end comprises a first annealed oligonucleotide that is not present at the second end. The second end may have a second annealed oligonucleotide having at least one difference as compared to the first annealed oligonucleotide, e.g., a nucleic acid sequence difference or difference in nucleic acid modification, e.g., difference in methylation, difference in an attached binding moiety (e.g., biotin), etc. Such asymmetric nucleic acids are generally referred to as being "asymmetrically-primed nucleic acids". Nucleic acids that are asymmetrically-primed can themselves be symmetrically-tagged, i.e., nucleic acids having adapters with identical sequences at both the first and the second end, or asymmetrically-tagged, i.e., having a first adapter attached to a first end and a second adapter attached to a second end where the first adapter and the second adapter have at least one nucleic acid composition difference. The nucleic acid composition difference between the first adapter and the second adapter can be any desired difference, including but not limited to one or more nucleic acid sequence difference (e.g., substitutions, deletions, insertions, inversions, rearrangements (e.g., a different order of functional domains), or any combination thereof), or a nucleic acid modification difference. In certain embodiments, and as detailed herein, symmetrically-tagged nucleic acids can be asymmetrically-primed by contacting them with a mixture of a first oligonucleotide and a second oligonucleotide that are both specific for the same primer binding site (i.e., they both have a sequence that is sufficiently complementary to a primer binding site in the adapter to anneal under appropriate hybridization conditions) but that have at least one difference (e.g., a different nucleic acid sequence and/or modification). In certain embodiments, and as detailed herein, asymmetrically-tagged nucleic acids include a first primer binding site at one end and a second primer binding site at the second end that bind to different oligonucleotide sequences. Thus, contacting such asymmetrically-tagged nucleic acids with a first oligonucleotide specific for the first primer binding site and a second oligonucleotide specific for the second nucleic acid binding site under appropriate hybridization conditions will result in an asymmetrically-primed nucleic acid.

By "binding pair" is meant any two moieties that specifically bind to each other under at least one binding condition. Members of binding pairs include, but are not limited to, complementary single-stranded nucleic acid sequences, biotin/avidin or biotin/streptavidin, antigen/antibody, hapten/antibody (e.g., digoxigenin/anti-digoxigenin antibody), ligand/receptor, digoxigenin, etc. (It is noted that the antigen/hapten binding fragment of an antibody may be employed rather than the entire antibody.)

By "linker" is meant a moiety that functions to attach a first functional element or moiety to another. With respect to attaching nucleic acid domains to each other or to distinct moieties, linkers could be additional nucleotide bases (DNA, RNA, PNA, etc.), peptides, carbon-chain, poly-ethyleneglycol spacers, etc. Attachment of functional elements/moieties with a linker can be covalent or non-covalent. No limitation in this regard is intended.

By "strand-displacing nucleic acid polymerase", "strand-displacing polymerase", and equivalents thereof is meant a nucleic acid polymerase that has both 5' to 3' template dependent nucleic acid synthesis activity and 5' to 3' strand displacement activity. Thus, when such polymerases encounter a double-stranded region of a template during nucleic acid synthesis it will displace the non-template strand while continuing nucleic acid synthesis on the template strand. On circular templates (e.g., templates having a double-stranded insert with hairpin adapters at both ends, as shown in the Figures), such polymerases can enter into rolling circle replication under suitable nucleic acid synthesis conditions. While any suitable strand-displacing nucleic acid polymerase can be used, in certain embodiments the polymerase is a phi29 (Φ29) DNA polymerase or a modified version thereof. Where modified recombinant Φ29DNA polymerase is employed, it can be homologous to a wild-type or exonuclease deficient Φ29 DNA polymerase, e.g., as described in U.S. Pat. No. 5,001,050 (titled "Φ29 DNA polymerase"), U.S. Pat. No. 5,198,543 (titled "PHI29 DNA polymerase), or U.S. Pat. No. 5,576,204 (titled "Φ29 DNA polymerase"), the full disclosures of which are incorporated herein by reference in their entirety for all purposes. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SFS, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases are described, for example, in U.S. Pat. Nos. 8,420,366 and 8,257,954, both entitled "Generation of modified polymerases for improved accuracy in single molecule sequencing", incorporated herein by reference in their entirety for all purposes. Other strand displacing polymerases can also be used, e.g. as described in U.S. Pat. No. 8,936,926 (titled "Active surface coupled polymerases"), US Pat. App. Pub. No. 2010/0260465 (titled "Protein engineering strategies to optimize activity of surface attached proteins"), and U.S. Pat. No. 8,921,086 (titled "Polymerases for nucleotide analogue incorporation"), each of which are hereby incorporated by reference herein in their entirety for all purposes. In certain embodiments, a polymerase/template complex generated according to aspects of the present disclosure is used directly in a sequencing-by-synthesis reaction, e.g., a SMRT® Sequencing reaction (Pacific Biosciences or California, Inc.).

I. GENERAL

As summarized above, the present disclosure is generally directed to improved methods for isolating asymmetrically-primed nucleic acids, compositions of such nucleic acids, and reagents and kits for performing the methods. The isolated asymmetrically-primed nucleic acids find use in a number of different downstream applications, including as templates for carrying out nucleic acid sequence analysis.

The methods described herein can be employed to isolate asymmetrically-primed nucleic acids from nucleic acid samples (e.g., nucleic acid libraries) that comprise symmetrically-tagged nucleic acids (nucleic acids that have identical adapters at each end) or that contain asymmetrically-tagged nucleic acid templates (nucleic acids that have a first adapter at one end and a second adapter at the other end, where the first and second adapters have at least one nucleic acid sequence/modification difference). In some embodiments, the nucleic acid sample contains a mixture of symmetrically-tagged and asymmetrically-tagged nucleic acids.

In general, the nucleic acid templates that are subjected to the isolation workflows described herein include a double-stranded region (e.g., a double-stranded nucleic acid insert) with a hairpin on at least one end. Hairpins can be generated using any suitable method. In some embodiments, a hairpin is generated on a double-stranded nucleic acid fragment by ligating a hairpin adapter to a compatible end of the fragment, e.g., via blunt-end or sticky-end ligation, as is known in the art. The ligation of a hairpin adapter creates a nucleic acid template comprising a single-stranded region on at least one end that connects the two strands of the double-stranded nucleic acid insert (connecting the 3' end of a first strand of the insert with the 5' end of the hybridized complementary strand of the insert). Other methods for generating a hairpin on a nucleic acid may be employed.

One or both ends of a nucleic acid template can have a hairpin. In certain embodiments, the nucleic acid templates have hairpin adapters at both ends thereby making the template nucleic acids in a cyclic form. Cyclic nucleic acids that find use in the present disclosure include SMRTBELL® templates, which are nucleic acids having a central double-stranded region, and having hairpin regions at each end of the double-stranded region. The preparation and use of cyclic templates such as SMRTBELL® templates, are described for example in U.S. Pat. No. 8,003,330 (titled "Error-free amplification of DNA for clonal sequencing") and U.S. Pat. No. 8,236,499 (titled "Methods and compositions for nucleic acid sample preparation") the full disclosures of which are hereby incorporated by reference herein for all purposes. One advantage of the SMRTBELL® template is that it can be made from a library of double-stranded nucleic acid, e.g. DNA, fragments. For example, a sample of genomic DNA can be fragmented into a library of DNA fragments, by known methods such as by shearing or by use of restriction enzymes. The library of DNA fragments can be ligated to hairpin adaptors at each end of the fragment to produce a library of SMRTBELL® templates. The hairpin adaptors provide single stranded regions within the hairpins. By using the same hairpin adaptor for all of the fragments, the hairpin adaptors provide a position for universal priming of all of the sequences.

The present disclosure provides a sample-preparation method for nucleic acid sequencing in which hairpin-containing nucleic acid templates are isolated that are asymmetrically-primed. This asymmetric priming enables many downstream applications, including sequencing the template from only one direction (not from both ends of the template). This is especially useful when sequencing circular templates in a sequencing-by-synthesis process where having multiple polymerases on a single template results in premature termination or other interference in the sequencing process. The improved primed templates allow for generating longer sequencing reads (i.e., longer read lengths) and thus would benefit many sequencing applications, including enabling improved barcode sequencing and deconvolution either by allowing analysis of barcodes that are far apart or by allowing multiple reads of one or more barcodes on a shorter circular template. Longer sequencing reads would also benefit genome assembly and full-length transcript sequencing methods.

In describing aspects of the methods disclosed herein, reference will be made to the Figures. It is to be understood that the Figures merely illustrate specific embodiments of the disclosed methods and are not intended to be limiting.

As summarized above, and described in further detail below, both symmetrically-tagged and asymmetrically-tagged nucleic acids find use as templates for generating and isolating asymmetrically-primed nucleic acid templates according to the present disclosure. In many aspects, the process for isolating asymmetrically-primed nucleic acid templates includes eluting templates immobilized to a solid support through hybridization to a capture primer by the strand displacement activity of a nucleic acid polymerase. This step not only results in isolation of the desired template, but also serves as a quality control step, ensuring that the eluted templates are capable of supporting nucleic acid synthesis through at least one or both strands of the double stranded insert region. This quality control step removes templates that are damaged and that would thus not be optimal for downstream processes, e.g., sequencing reactions including single molecule sequencing reactions (e.g., SMRT® Sequencing or nanopore sequencing).

II. GENERATING NUCLEIC ACID TEMPLATES

The general method typically begins with double-stranded nucleic acid fragments having defined ends, which could be blunt ends or ends with known overhang sequences (5' or 3' overhangs). These nucleic acid fragments can be of any size or size range and can include DNA, RNA, DNA-RNA hybrids (e.g., molecules produced by first-strand synthesis during cDNA prep have one mRNA strand and one complementary DNA strand), genomic DNA, cDNA, mRNA, tRNA, etc. In some embodiments, the nucleotide sequence of the fragments is not known.

In certain embodiments, the double-stranded nucleic acid fragments used in methods and compositions of the present disclosure comprise nucleic acids obtained from a sample. The sample may comprise any number of things, including, but not limited to: bodily fluids (including, but not limited to, blood, urine, serum, lymph, saliva, anal and vaginal secretions, perspiration and semen) and cells of virtually any organism (e.g., mammalian species including humans); environmental samples (including, but not limited to, air, agricultural, water and soil samples); biological warfare agent samples; research samples; the products of an amplification reaction (including both target and signal amplification, such as PCR amplification reactions); purified samples (e.g., such as purified genomic DNA, raw samples (bacteria, virus, genomic DNA, etc.)). As will be appreciated by those in the art, virtually any experimental manipulation may have been done on the samples.

Genomic DNA, when used in the disclosed methods, can be prepared from any source by three steps: cell lysis, deproteinization and recovery of DNA. These steps are adapted to the demands of the application, the requested yield, purity and molecular weight of the DNA, and the amount and history of the source. Further details regarding the isolation of genomic DNA can be found in Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2008 ("Sambrook"); Current Protocols in Molecular Biology, F. M. Ausubel et al., eds., Current Protocols, a joint venture between Greene Publishing Associates, Inc. and John Wiley & Sons, Inc ("Ausubel"); Kaufman et al. (2003) Handbook of Molecular and Cellular Methods in Biology and Medicine Second Edition Ceske (ed) CRC Press (Kaufman); and The Nucleic Acid Protocols Handbook Ralph Rapley (ed) (2000) Cold Spring Harbor, Humana Press Inc (Rapley). In addition, many kits are commercially available for the purification of genomic DNA from cells, including Wizard™ Genomic DNA Purification Kit, available from Promega; Aqua Pure™ Genomic DNA Isolation Kit, available from BioRad; Easy-DNA™ Kit, available from Invitrogen; and DnEasy™ Tissue Kit, which is available from Qiagen. Alternatively, or additionally, target nucleic acid segments may be obtained through targeted capture protocols where target nucleic acids are obtained initially as single stranded segments on microarrays or other capture techniques, followed by amplification of the captured material to generate double stranded sample materials. A variety of such capture protocols have been described in, e.g., Hodges E, et al. Nat. Genet. 2007 Nov. 4, Olson M., Nature Methods 2007 November; 4(11):891-2, Albert T J, et al. Nature Methods 2007 November; 4(11):903-5, and Okou D T, et al. Nature Methods 2007 November; 4(11):907-9.

Nucleic acids that can be used in the methods described herein can also be derived from a cDNA, e.g. cDNAs prepared from mRNA obtained from, e.g., a eukaryotic subject or a specific tissue derived from a eukaryotic subject. Data obtained from sequencing the nucleic acid templates derived from a cDNA library, e.g., using a high-throughput sequencing system, can be useful in identifying, e.g., novel splice variants of a gene of interest or in comparing the differential expression of, e.g., splice isoforms of a gene of interest, e.g., between different tissue types, between different treatments to the same tissue type or between different developmental stages of the same tissue type.

mRNA can typically be isolated from almost any source using protocols and methods described in, e.g., Sambrook and Ausubel. The yield and quality of the isolated mRNA can depend on, e.g., how a tissue is stored prior to RNA extraction, the means by which the tissue is disrupted during RNA extraction, or on the type of tissue from which the RNA is extracted. RNA isolation protocols can be optimized accordingly. Many mRNA isolation kits are commercially available, e.g., the mRNA-ONLY™ Prokaryotic mRNA Isolation Kit and the mRNA-ONLY™ Eukaryotic mRNA Isolation Kit (Epicentre Biotechnologies), the FastTrack 2.0 mRNA Isolation Kit (Invitrogen), and the Easy-mRNA Kit (BioChain). In addition, mRNA from various sources, e.g., bovine, mouse, and human, and tissues, e.g. brain, blood, and heart, is commercially available from, e.g., BioChain (Hayward, Calif.), Ambion (Austin, Tex.), and Clontech (Mountainview, Calif.).

Once the purified mRNA is recovered, reverse transcriptase is used to generate cDNAs from the mRNA templates. Methods and protocols for the production of cDNA from mRNAs, e.g., harvested from prokaryotes as well as eukaryotes, are elaborated in *cDNA Library Protocols*, I. G. Cowell, et al., eds., Humana Press, New Jersey, 1997, Sambrook and Ausubel. In addition, many kits are commercially available for the preparation of cDNA, including the Cells-to-cDNA™ II Kit (Ambion), the RETROscript™ Kit (Ambion), the CloneMiner™ cDNA Library Construction Kit (Invitrogen), and the Universal RiboClone® cDNA Synthesis System (Promega). Many companies, e.g., Agencourt Bioscience and Clontech, offer cDNA synthesis services.

In some embodiments of the invention described herein, nucleic acid fragments are generated from a genomic DNA or a cDNA. There exists a plethora of ways of generating nucleic acid fragments from a genomic DNA, a cDNA, or a DNA concatemer. These include, but are not limited to, mechanical methods, such as sonication, mechanical shearing, nebulization, hydroshearing, and the like; chemical methods, such as treatment with hydroxyl radicals, Cu(II): thiol combinations, diazonium salts, and the like; enzymatic methods, such as exonuclease digestion, restriction endonuclease digestion, and the like; and electrochemical cleavage. These methods are further explicated in Sambrook and Ausubel.

In further embodiments, nucleic acid molecules are obtained from a sample and fragmented for use in methods of the present disclosure. The fragments may further be modified in accordance with any methods known in the art and described herein. Nucleic acid fragments may be generated by fragmenting source nucleic acids, such as genomic DNA, using any method known in the art. In one embodiment, shear forces during lysis and extraction of genomic DNA generate fragments in a desired range. Also encompassed by the invention are methods of fragmentation utilizing restriction endonucleases.

Double-stranded nucleic acid fragments can be any length that is desired for subsequent uses, e.g., cloning, sequencing, transformation, enrichment, etc. In certain embodiments, the fragments can be from about 10 to about 50,000 base pairs (bp) in length and any ranger therebetween, e.g., from about 100 to about 40,000 bp, from about 300 to 30,000 bp, from about 500 to 20,000 bp, from about 800 to 10,000 bp, from about 1,000 to 8,000 bp, etc. In certain embodiments, the average size of the double-stranded nucleic acid fragments is at least about 100 bp in length, at least about 200, at least about 300, at least about 500, at least about 1,000, at least about 1,500, at least about 2,000, at least about 5,000, at least about 10,000, at least about 20,000, etc.

In certain embodiments, the fragments are treated to produce blunt ends that are compatible with ligation to a first adapter having a compatible blunt end. Any suitable method for producing blunt ends may be employed, including treatment with one or more enzyme having 5' and/or 3' single strand exonuclease activity (e.g., *E. coli* Exonuclease III) and/or performing a fill-in reaction to extend 3' recessed ends (e.g., with T4 DNA polymerase). No limitation in this regard is intended.

The method can entail first fragmenting a double stranded DNA sample into double stranded fragments, then ligating to each end of the double stranded fragments a hairpin to produce a population of functionally circular DNA templates having a central double stranded region and hairpin regions on each end. The hairpin regions on each end include single stranded regions that can be used for both priming and capture. Generation and use of such functionally circular constructs has been described in U.S. Pat. No. 8,236,499 (titled "Methods and compositions for nucleic acid sample preparation") and U.S. Pat. No. 8,153,375 (titled "Compositions and methods for nucleic acid sequencing"), the full disclosures of which are hereby incorporated by reference herein in their entirety for all purposes. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

Figure 3:
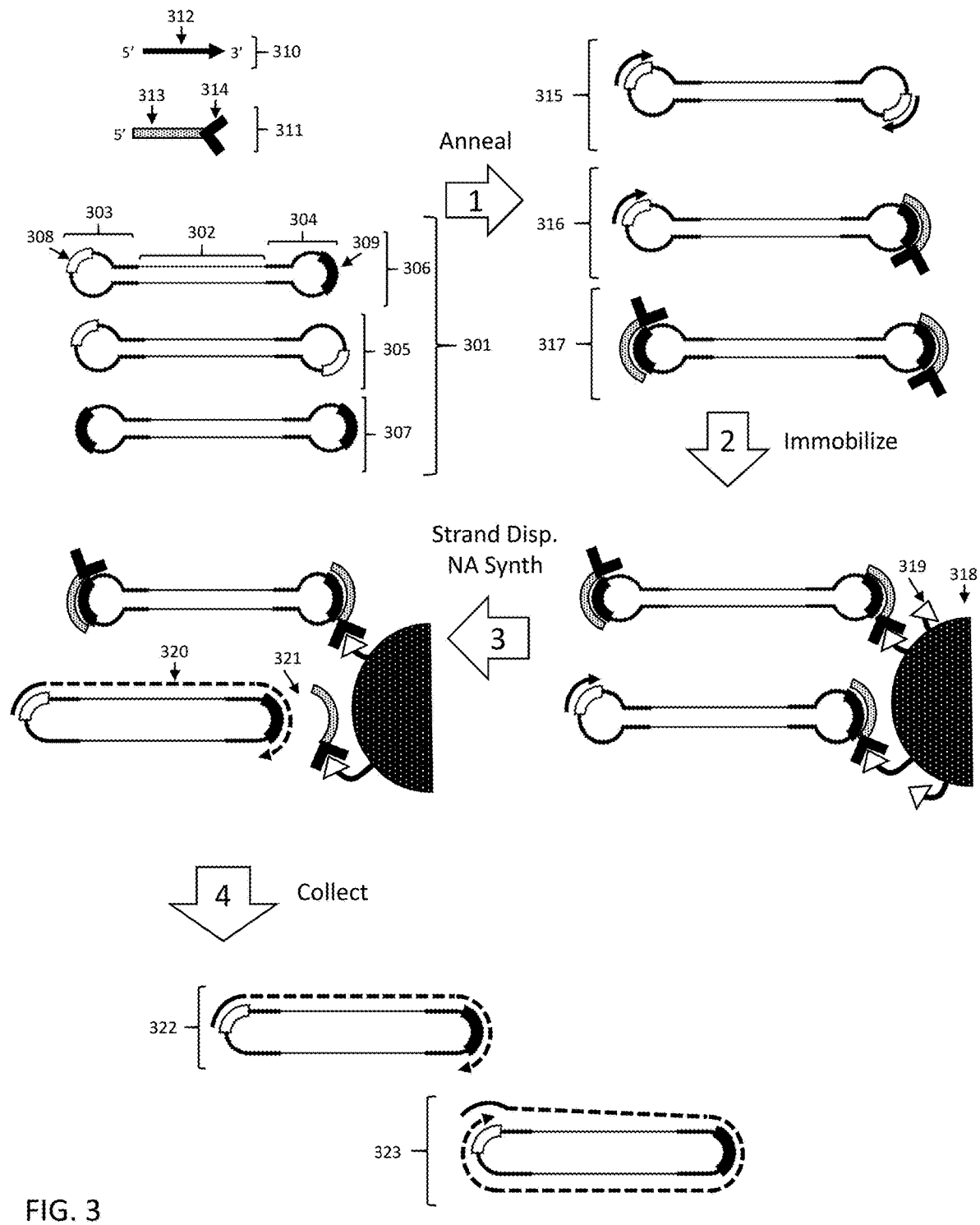
FIG. 3 illustrates an embodiment of a workflow for isolating asymmetrically-primed nucleic acids from a nucleic acid sample comprising a mixture of symmetrically-tagged and asymmetrically-tagged nucleic acid templates using strand displacement nucleic acid synthesis.

DNA species with hairpin adapters at both ends can be symmetric (same hairpin adapter at both ends) or asymmetric (the hairpin adapter at one end is different from the hairpin adapter at the other end). In making asymmetric DNA templates, two different hairpin adapters (adapters 1 and 2) can be mixed and ligated to a pool of double stranded nucleic acids simultaneously. This process can generate a sample that contains the desired asymmetric species but also undesired symmetric species (e.g., as shown in FIG. 3; population 301). Other undesired species may also be present, e.g., those with no or only one adapter (not shown in FIG. 3).

Any method for making a desired nucleic acid sample that finds use in the disclosed methods can be used. Alternatively, a user may obtain a desired nucleic acid sample from a third party.

III. SYMMETRICALLY-TAGGED NUCLEIC ACID TEMPLATES

FIG. 1 shows an example of a workflow for isolating an asymmetrically-primed nucleic acid. In this workflow, a sample comprising symmetrically-tagged nucleic acid templates (101) is obtained in any suitable manner (e.g., as described elsewhere herein). The symmetrically-tagged nucleic acid templates have an insert region (102) flanked by identical terminal adapter regions (103) that include at least one primer binding site (104) (the adapters can include other regions, e.g., barcodes, second primer binding sites, etc.).

In step 1, the sample is contacted under nucleic acid hybridization conditions with a first primer (105) and a second primer (106) that include a region (107 and 108, respectively) that hybridizes to the primer binding site (104) in the adapter regions of the symmetrically tagged nucleic acid templates in the sample under hybridization conditions. While in general the nucleic acid sequence of regions (107) and (108) are identical, in some embodiments they are not identical. Where the nucleic acid sequences of regions (107) and (108) are not identical, they are designed such that only one can bind to a given primer binding site at a time (i.e., they compete for binding to the primer binding site).

In addition to region (107), first primer (105) also includes a cleavage site (109) and first capture region (110) that are positioned 5' to region (107). Because of this orientation, when region (107) of primer (105) is bound to its cognate primer binding site (104) in a template (101), it provides an initiation site for nucleic acid synthesis by a nucleic acid polymerase under nucleic acid synthesis conditions. In certain embodiments, the primer (105) (sometimes referred to as a "synthesis primer") is complexed with a polymerase prior to contacting with the nucleic acid sample, while in other embodiments a polymerase is added in a later step as desired (not shown). Polymerization from the synthesis primer when a polymerase is present can be prevented in the workflow until such time as this activity is desired (see below). Any suitable methods for preventing nucleic acid synthesis from the annealed synthesis primer/polymerase complex may be employed. For example, one or more dNTPs and/or divalent cation co-factors can be absent from buffers until nucleic acid synthesis is desired. In addition, or alternatively, a synthesis blocking moiety can be removed from the annealed synthesis primer/polymerase complex, e.g., a 3'-terminal dideoxy-nucleotide or non-complementary nucleotide on the primer. No limitation in this regard is intended.

In addition to region (108), second primer (106) includes second capture region (111) that is positioned 3' to region (108). Because of this orientation of regions (108) and (111), primer (106) does not serve as an initiation site for nucleic acid synthesis by a polymerase when bound to its cognate primer binding site (104). Specifically, capture region (111) is designed to not hybridize to the primer binding site (104) or regions adjacent to it in template (101) in a synthesis-competent manner. As their names suggest, the capture regions (110) and (111) are designed to allow for the capture of complexes that contain it, e.g., nucleic acid templates hybridized to primer (105) [for first capture region (110)] or primer (106) [for second capture region (111)]. In general, the capture region can be considered a first member of a binding pair. Moreover, capture regions (110) and (111) are selected so as not to bind to the same capture moiety (or binding partner), and thus allow for differential binding of complexes containing primer (105) versus primer (106). In certain embodiments, the capture tag is a region of the primer that does not hybridize to the primer binding site (104) in the adapter (or other sequences in template nucleic acid) and thus remains single stranded once the region specific for the primer binding site in the primer is hybridized to the primer binding site. This region can be a DNA sequence, a RNA sequence, a combination of DNA and RNA, and/or contain nucleotide bases other than A, G, C, T and U (e.g., inosine). In other embodiments, the capture tag comprises a non-oligonucleotide capture tag, including but not limited to avidin, streptavidin, biotin, digoxigenin, an antigen, an antibody or fragment thereof, etc. In some embodiments, the capture region is connected to the primer binding site-specific region of the capture primer by a linker moiety. Any suitable linker may be employed, including but not limited to an additional nucleotide sequence (e.g., DNA, RNA, etc.), peptides, carbon-chain, poly-ethylene-glycol spacers, and the like.

Because the primers (105) and (106) bind competitively to the primer binding sites (104) in the symmetrically-tagged nucleic acid templates, three distinct species of primer-hybridized nucleic acid template complexes are produced in the contacting step (excluding templates that only have one or no hybridized primer). Two of the complexes are symmetrically primed with either primer (105) (complex 113) or primer (106) (complex 114), which have the same primer hybridized to both terminal adapters, while one of the complexes is asymmetrically primed (complex 112), which has first primer (105) at one end and second primer (106) at the other end. In order to maximize the desired asymmetrically-primed species, the synthesis primer and the capture primer are designed to have similar hybridization characteristics, are present at about a 1:1 molar ratio when contacted to the nucleic acid sample, and are in molar excess with respect to the total number of primer binding sites in the sample. Suitable ranges for these parameters are routinely determined in the relevant art.

In step 2, the sample containing the three primer-hybridized nucleic acid template complexes (112, 113, and 114) is contacted to a solid support (115) with immobilized cognate binding partners for the first capture region (116) under conditions that allow for binding between the first capture region (110) and its cognate binding partner (116). Given the variety of capture regions that can be employed (as noted above), the binding mechanism can include one or more of nucleic acid hybridization, biotin/streptavidin binding, antibody/antigen binding, receptor/ligand binding, etc. No limitation in this regard is intended. The solid support can be any suitable material in any suitable form, including surface modified beads, resins, nanoparticles, or planar surfaces with the corresponding binding chemistry. Out of the three primer-hybridized nucleic acid template complexes (112, 113, and 114), only the two with the first primer (105) hybridized thereto can bind, via the capture region (110), to the immobilized binding partner (complexes 112 and 113). The remaining complex (114), which has no first primer (105) hybridized thereto, is removed from the mixture as supernatant (e.g., during a washing step).

In step 3, the immobilized complexes are then eluted from solid support (115) by contact with an agent that cleaves at cleavage site (109) in primer (105). Any suitable cleavage site/cleavage reagent combination can be used. For example, where the cleavage site (109) is a disulfide linker, the immobilized complexes can be contacted with dithiothreitol (DTT). Alternatively, where the cleavage site (109) in primer (105) is a unique restriction enzyme recognition site, the immobilized complexes can be contacted with the cognate restriction enzyme. No limitation in this regard in intended. The eluted sample includes symmetrically-primed nucleic acid complexes (117), which have primer region (107) annealed to primer binding site (104) at both ends, and asymmetrically primed nucleic acid complexes (118), which have primer region (107) annealed to primer binding site (104) at a first end and second primer (106) annealed at the primer binding site (104) at the second (opposite) end.

In step 4, The eluted sample is then contacted to a second solid support (119) with immobilized cognate binding partners for the second capture region (120) under conditions that allow for binding between the second capture region (111) and its cognate binding partner (119). The remaining species (117), which has no second primer (106) hybridized thereto, is removed from the mixture as supernatant (e.g., during a washing step). The resulting isolated asymmetrically-primed nucleic acid complex (118) can then be used as desired, either while immobilized on the solid support or after it is eluted.

In many embodiments, the isolated asymmetrically-primed nucleic acid complex is used as a template in a nucleic acid sequencing reaction that employs hybridized primer region (107) as the sequencing primer (as it is synthesis competent). For example, the immobilized template can be loaded into a zero-mode waveguide and sequenced in a Single Molecule, Real-Time Sequencing assay (SMRT® Sequencing from Pacific Biosciences of California, Inc.), e.g., as described in U.S. Pat. No. 7,315,019 entitled "Arrays of optical confinements and uses thereof"; U.S. Pat. No. 8,153,375 entitled "Compositions and methods for nucleic acid sequencing"; U.S. Pat. No. 8,658,364, entitled "Isolation of polymerase-nucleic acid complexes"; and U.S. Pat. No. 9,175,341 entitled "Methods for identifying nucleic acid modifications"; each of which is hereby incorporated by reference herein in its entirety.

Figure 2:
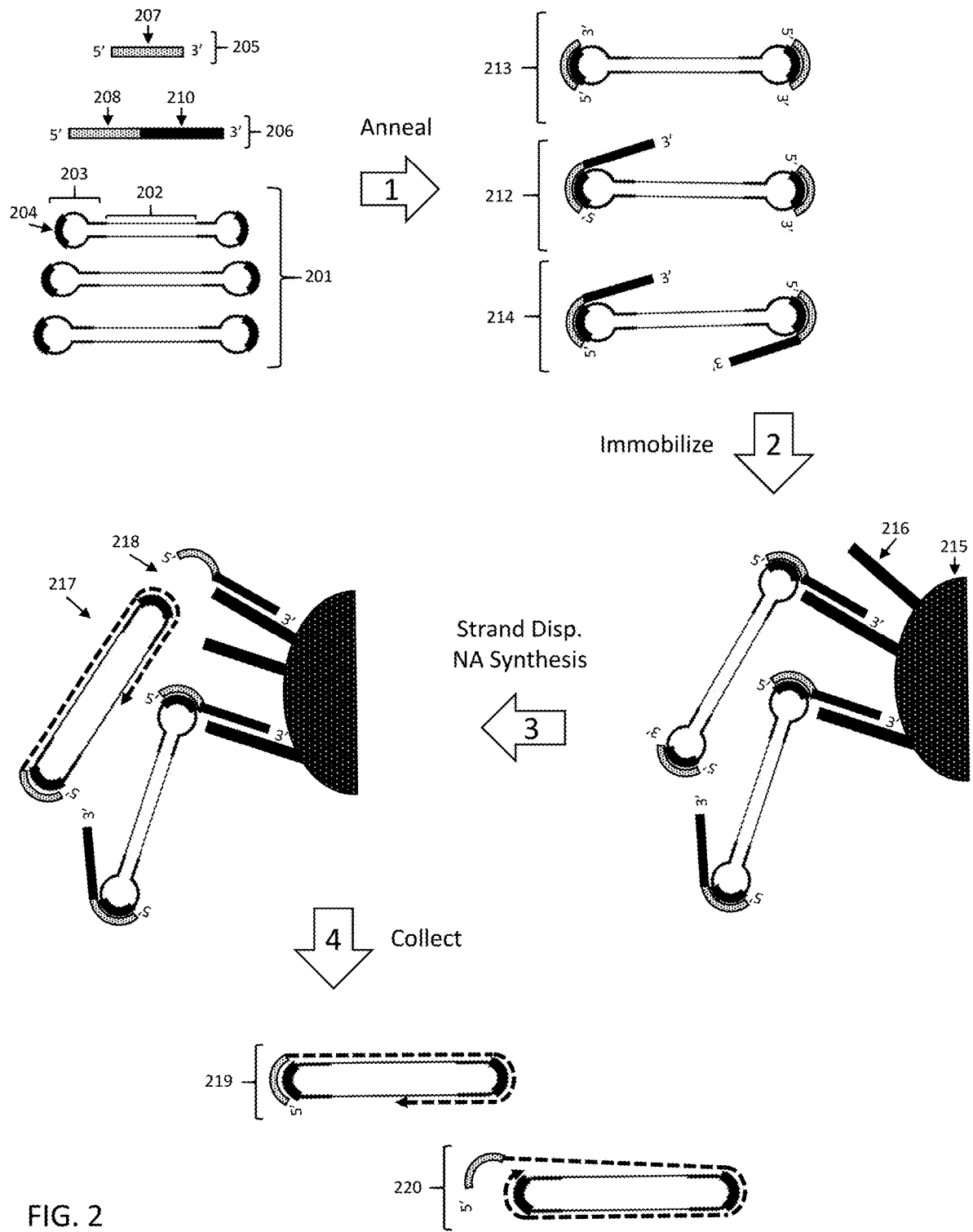
FIG. 2 illustrates an embodiment of a workflow for isolating asymmetrically-primed nucleic acids from a nucleic acid sample comprising symmetrically-tagged nucleic acid templates using strand displacement nucleic acid synthesis.

FIG. 2 shows another embodiment of a workflow for isolating asymmetrically-primed nucleic acid. As in the previous embodiment as exemplified in FIG. 1, a sample comprising symmetrically-tagged nucleic acid templates (201) is obtained in any suitable manner. The symmetrically tagged nucleic acid templates have an insert region (202) flanked by identical terminal adapter regions (203) that include at least one primer binding site (204) (the adapters can include other regions, e.g., barcodes, second primer binding sites, etc.).

In step 1, the sample is contacted under nucleic acid hybridization conditions with a nucleic acid synthesis primer (or "synthesis primer") (205) and a capture primer (206) that are both specific for the primer binding site (204) in the adapter region of the symmetrically-tagged nucleic acids. Thus, both the synthesis primer and the capture primer include a region (207 and 208, respectively) that hybridizes to the primer binding site (204) in the adapter regions of the symmetrically tagged nucleic acid templates in the sample under hybridization conditions. While in general the nucleic acid sequence of regions (207) and (208) are identical, in some embodiments they are not identical. Where the nucleic acid sequences of regions (207) and (208) are not identical, they are designed such that only one can bind to a given primer binding site at a time (i.e., they compete for binding to the primer binding site). The synthesis primer, as its name implies, is able to serve as an initiation site for nucleic acid synthesis by a nucleic acid polymerase when bound to its cognate primer binding site. In certain embodiments, the synthesis primer is complexed with a polymerase prior to or during contacting with the nucleic acid sample, while in other embodiments a polymerase is added to the contacted sample after hybridization of the synthesis primer has occurred (polymerase is not shown in FIG. 2). Polymerization from the synthesis primer is prevented in the workflow until such time as this activity is desired (see below). Any suitable methods for preventing nucleic acid synthesis from the annealed synthesis primer/polymerase complex may be employed. For example, one or more dNTPs and/or divalent cation co-factors can be absent from buffers until nucleic acid synthesis is desired. In addition, or alternatively, a synthesis blocking moiety can be removed from the annealed synthesis primer/polymerase complex, e.g., a 3'-terminal dideoxy-nucleotide or non-complementary nucleotide on the primer. No limitation in this regard is intended.

As shown in FIG. 2, capture primer (206) includes a capture region (210) that is designed to allow for the capture and isolation of complexes that contain it, e.g., nucleic acid templates hybridized via region (208) to the capture primer. In general, capture region (210) can be considered a first member of a binding pair. In certain embodiments, capture region (210) is an oligonucleotide region of capture primer (206) that does not hybridize to the primer binding site (204) or regions adjacent to it in adapter (203) (or other sequences in template nucleic acid) and thus remains single stranded when region (208) in the capture primer (206) is hybridized to the primer binding site (204). This region can be a DNA sequence, a RNA sequence, a combination of DNA and RNA, and/or contain nucleotide bases other than A, G, C, T and U (e.g., inosine). In other embodiments, the capture region comprises a non-oligonucleotide binding moiety, including but not limited to avidin, streptavidin, biotin, digoxigenin, an antigen, an antibody or fragment thereof, etc. In some embodiments, the capture region is connected to the primer binding site-specific region of the capture primer by a linker moiety. Any suitable linker may be employed, including but not limited to an additional nucleotide sequence (e.g., DNA, RNA, etc.), peptides, carbon-chain, poly-ethylene-glycol spacers, and the like. The capture region, with or without a linker, can be present at any suitable location on the capture primer, e.g., the 5' end, the 3' and or at an internal site of the capture primer. In some embodiments, the linker moiety and/or the capture region serves as a nucleic acid synthesis blocking moiety, e.g., being present at the 3' end of the nucleic acid sequence in the capture primer.

In contrast to synthesis primer (205), and as eluded to above, capture primer (206) is designed not to serve as an initiation site for nucleic acid synthesis by a polymerase when bound to its cognate primer binding site. Any suitable design scheme for such a synthesis-deficient primer may be employed, including having one or more non-complementary nucleotides at the 3' terminus of the capture primer (e.g., capture region 210). As another example, the capture primer can include a nucleic acid synthesis blocking moiety at the 3' terminus, e.g., a non-nucleotide blocking moiety, a dideoxy-nucleotide, an abasic nucleotide, and the like. No limitation in this regard is intended.

Because the synthesis primer and the capture primer bind competitively to the primer binding site in the symmetric nucleic acid templates, three distinct primer-hybridized nucleic acid template complexes are produced in the contacting step (excluding templates that only have one or no hybridized primer). Two of the complexes are symmetrically primed with either the synthesis primer (complex 213) or the capture primer (complex 214), which have the same primer hybridized to both terminal adapters, while one of the complexes is asymmetrically-primed (complex 212), which has a synthesis primer at one end and a capture primer at the other end. In order to maximize the desired asymmetrically-primed nucleic acid template complex, the synthesis primer and the capture primer are designed to have similar hybridization characteristics, are present at about a 1:1 molar ratio when contacted to the nucleic acid sample, and are in molar excess with respect to the total number of primer binding sites in the sample. Suitable ranges for these parameters are routinely determined in the relevant art.

In step 2, the sample containing the three primer-hybridized nucleic acid template complexes (212, 213, and 214) is contacted to a solid support (215) with immobilized cognate binding partners for the capture region (216) under conditions that allow for binding between the capture region and its cognate binding partner. Given the variety of capture regions that can be employed (as noted above), the binding mechanism can include one or more of nucleic acid hybridization, biotin/streptavidin binding, antibody/antigen binding, receptor/ligand binding, etc. No limitation in this regard is intended. The solid support can be any suitable material in any suitable form, including surface modified beads, resins, nanoparticles, or planar surfaces with the corresponding binding chemistry. Out of the three primer-hybridized nucleic acid template complexes (212, 213, and 214), only the two with the capture primer hybridized thereto can bind, via the capture region (210), to the immobilized binding partner (212 and 214). The remaining complex (213), which has no capture primer hybridized thereto, is removed from the mixture as supernatant (e.g., during a washing step).

In step 3, the solid support is contacted with a nucleic acid synthesis reagent mixture that supports nucleic acid synthesis by a strand-displacing nucleic acid polymerase from the hybridized synthesis primer. As noted above, the polymerase can be complexed with the synthesis primer in the previous steps. In other embodiments, however, the polymerase can be added at any suitable time after hybridization of the synthesis primer, e.g., before, during, or after contacting to the solid support. Because only the asymmetrically-primed nucleic acid template complex (212) includes a hybridized synthesis primer (205), nucleic acid synthesis (shown as dotted line 217) can only proceed from this complex bound to the solid support (nucleic acid synthesis cannot be initiated form the symmetrically-tagged nucleic acid template complex (214) because it has two capture primers hybridized to it). In addition to 5' to 3' nucleic acid synthesis activity, strand displacing nucleic acid polymerases employed in this method also have 5' to 3' strand displacement activity. Thus, once the polymerase has proceeded through the insert region of the nucleic acid template it will encounter the hybridized capture primer in the adapter at the opposite end of the template and displace it from the primer binding site (218). Thus, this process results in the targeted release of asymmetrically-primed nucleic acid template complexes from the solid support and into the supernatant, while symmetrically-primed nucleic acid templates having capture primers hybridized at both ends remain immobilized, thereby isolating asymmetrically-primed nucleic acid templates (step 4, complexes 219 and 220).

Because the activity of a strand displacing nucleic acid polymerase is used to elute the desired templates from the solid support, any template that is incapable of supporting nucleic acid synthesis at any location upstream of the hybridized capture primer will not be eluted. For example, an asymmetrically-primed nucleic acid template that is damaged in the insert region upstream of the hybridized capture primer (e.g., has an abasic residue, nick, gap, etc.) will not support nucleic acid synthesis and thus will not be eluted even though nucleic acid synthesis was initiated by the polymerase at the annealed synthesis primer. This process thus serves as an additional quality control step for the nucleic acid template, and is especially useful when the isolated templates are being used for subsequent sequence analysis (especially single molecule sequence analyses, e.g., SMRT® Sequencing and nanopore-based sequencing). In certain embodiments, the nucleic acid synthesis reaction is allowed to continue on the asymmetrically primed template after elution from the solid support. In certain embodiments, the nucleic acid synthesis reaction is allowed to continue until it has traversed the entire template, including both strands of the insert and both adapter regions, and enters into rolling circle amplification (220). Once the nucleic acid synthesis reaction has continued for the desired amount of time, it can be stopped by any suitable method, e.g., by chemical or physical means.

The isolated asymmetrically-primed nucleic acid templates can be employed in one or more analytical reactions or processes as desired by a user, including nucleic acid sequence analysis (as noted above). Sequence analysis can be performed on the nucleic acid template itself and/or a nascent nucleic acid strand synthesized from the template (e.g., the nucleic acid strand synthesized by the strand-displacing nucleic acid polymerase used to elute the asymmetrically-primed nucleic acid template). In certain embodiments, the isolated asymmetrically-primed nucleic acid templates can be subjected to additional enrichment/isolation processes, e.g., processing to isolate nucleic acid templates comprising one or more regions of interest in the insert region of the template.

IV. ASYMMETRICALLY-TAGGED NUCLEIC ACID TEMPLATES

FIG. 3 provides another workflow for isolating asymmetrically-primed nucleic acid template complexes. In contrast to the workflows in FIGS. 1 and 2, the asymmetrically-primed nucleic acid templates isolated in FIG. 3 are asymmetrically-tagged rather than symmetrically-tagged.

The nucleic acid sample (301) includes a mixture of nucleic acid templates comprising double-stranded nucleic acid inserts (302) and terminal adapters selected from first adapter (303) and second adapter (304). Adapter (303) and (304) are different, meaning that they have at least one nucleic acid difference when compared to each other (e.g., different primer binding sites). Nucleic acid sample (301) comprises at least 3 different nucleic acid templates structures: symmetrically-tagged nucleic acid templates (305) and (307), which include the same adapter at opposite ends (adapter (303) in species (305) and adapter (304) in species (307)) and asymmetrically-tagged nucleic acid template (306), which includes a first adapter at one end (303) and a second adapter at the opposite end (304). It is noted here that additional undesired template species may also be present in the sample, e.g., those with no or only one adapter, but are not shown for simplicity. Adapter (303) and (304) each include at least one primer binding site ((308) and (309), respectively) that anneal to different cognate primers, i.e., they hybridize to different primer sequences under at least one/a range of suitably stringent nucleic acid hybridization conditions. The adapters (303) and (304) can include other regions in addition to the primer binding sites (308) and (309), including but not limited to barcodes, additional distinct primer binding sites, promoters, restriction enzyme sites, etc.

In step 1, sample (301) is contacted under nucleic acid hybridization conditions with a nucleic acid synthesis primer (or "synthesis primer") (310) that is specific for primer binding site 308 (which can thus be considered a synthesis primer binding site) and a capture primer (311) that is specific for primer binding site 309 (which can thus be considered a capture primer binding site). Thus, the synthesis primer 310 and the capture primer 311 each include a region (312 and 313, respectively) that hybridizes to their cognate primer binding sites (308 and 309, respectively) in the adapter regions of the nucleic acid templates in the sample under suitably stringent hybridization conditions. Similar to the workflow in FIG. 2, the synthesis primer, as its name implies, is able to serve as an initiation site for nucleic acid synthesis by a polymerase when bound to its cognate primer binding site (indicated by the presence of an arrow). In certain embodiments, the synthesis primer is complexed with a polymerase prior to contacting with the nucleic acid sample, while in other embodiments a polymerase is added to the contacted sample after hybridization of the synthesis primer has occurred (polymerase is not shown). Polymerization from the synthesis primer is prevented in the workflow until such time as this activity is desired (see below). Also, similar to the workflow in FIG. 2, the capture primer is designed not to serve as an initiation site for nucleic acid synthesis by a polymerase when bound to its cognate primer binding site. Any suitable design scheme for such a synthesis-deficient primer may be employed, including having one or more non-complementary nucleotides at the 3' terminus of the capture primer or other non-nucleotide synthesis blocking moiety. For example, the capture primer can include a nucleic acid synthesis blocking moiety at the 3' terminus, e.g., a dideoxynucleotide, abasic nucleotide, and the like. As its name implies, the capture primer is designed to allow for the capture and isolation of complexes that contain it, e.g., nucleic acid templates hybridized to the capture primer, via a capture moiety (314). Because the synthesis primer and the capture primer bind to unique primer binding sites in the different adapters on the templates, three distinct species of primed nucleic acid template complexes are produced in the contacting step (315, 316 and 317) corresponding to the three different species of nucleic acid template present in the sample (305, 306, and 307, respectively). Because templates (305) and (307) have identical adapters at both ends, the same primer hybridizes to each end: primed nucleic acid template complex (315) having two hybridized synthesis primers and primed nucleic acid template complex (317) having two hybridized capture primers. In contrast, because template (306) has a different adapter at each end, primed nucleic acid template complex (316) has a capture primer hybridized at one end and a synthesis primer hybridized at the other. Nucleic acid complex (316) is thus asymmetrically primed while nucleic acid complexes (315) and (317) are symmetrically primed.

In step 2, the sample containing the three primed nucleic acid template complexes (315, 316, and 317) is contacted to a solid support (318) with immobilized cognate binding partners for the capture moiety (319) under conditions that allow for binding between the capture moiety and its cognate binding partner. Given the variety of capture moieties that can be employed (as noted above), the binding mechanism can include one or more of nucleic acid hybridization, biotin/streptavidin binding, antibody/antigen binding, receptor/ligand binding, etc. No limitation in this regard is intended. The solid support can be any suitable material in any suitable form, including surface modified beads, resins, nanoparticles, or planar surfaces with the corresponding binding chemistry. Out of the three primer-hybridized nucleic acid template complexes (315, 316, and 317), only the two with the capture primer hybridized thereto can bind to the cognate binding partner (319) via the capture moiety (314). The remaining nucleic acid template complex (315), which has no capture primer hybridized thereto, is removed from the mixture as supernatant (e.g., during a washing step).

In step 3, the solid support is contacted with a nucleic acid synthesis reagent mixture that supports nucleic acid synthesis by a strand-displacing nucleic acid polymerase from the hybridized synthesis primer. As noted above, the polymerase can be complexed with the synthesis primer in the previous steps. In other embodiments, however, the polymerase can be added at any suitable time after hybridization of the synthesis primer, e.g., before, during, or after contacting to the solid support. Because only the asymmetrically-primed nucleic acid template complex (316) includes a hybridized synthesis primer (310), nucleic acid synthesis (shown as dotted line 320) can only proceed from this complex bound to the solid support (nucleic acid synthesis cannot be initiated form the symmetrically-tagged nucleic acid template complex (317) because it has two capture primers hybridized to it). In addition to 5' to 3' nucleic acid synthesis activity, strand-displacing nucleic acid polymerases employed in this method also have 5' to 3' strand displacement activity. Thus, once the polymerase has proceeded through the insert region of the nucleic acid template it will encounter the hybridized capture primer in the adapter at the opposite end of the template and displace it from the primer binding site (321). Thus, this process results in the targeted release of asymmetrically-primed nucleic acid template complexes from the solid support and into the supernatant, while symmetrically-primed nucleic acid templates having capture primers hybridized at both ends remain immobilized, thereby isolating asymmetrically-primed nucleic acid templates (step 4, complexes 322 and 323).

Because the activity of a strand displacing polymerase is used to elute the desired templates from the solid support, any template that is incapable of supporting nucleic acid synthesis at any location upstream of the hybridized capture primer will not be eluted. For example, an asymmetrically-primed template that is damaged in the insert region upstream of the hybridized capture primer (e.g., has an abasic residue, nick, gap, etc.) will not support nucleic acid synthesis and thus will not be eluted even though nucleic acid synthesis was initiated by the polymerase at the annealed synthesis primer. This process thus serves as an additional quality control step for the template, and is especially useful when the isolated templates are being used for subsequent sequence analysis (especially single molecule sequence analyses, e.g., SMRT® sequencing and nanopore-based sequencing). In certain embodiments, the nucleic acid synthesis reaction is allowed to continue on the asymmetrically primed template after elution from the solid support. In certain embodiments, the nucleic acid synthesis reaction is allowed to continue until it has traversed the entire template, including both strands of the insert and both adapter regions, and enters into rolling circle amplification (323). Once the nucleic acid synthesis reaction has continued for the desired amount of time, it can be stopped by any suitable method, e.g., by chemical or physical means.

The isolated asymmetrically-primed nucleic acid template complexes can be employed in one or more analytical reactions or processes as desired by a user, including nucleic acid sequence analysis. In certain embodiments, the isolated asymmetrically-primed nucleic acid template complexes can be subjected to additional enrichment/isolation processes, e.g., processing to isolate nucleic acid templates comprising one or more regions of interest in the insert region of the template.

Modifications to the workflow in FIG. 3 can be made that still result in isolation of asymmetrically primed nucleic acid template complexes. As one example, the nucleic acid sample can be contacted with the capture primer alone under hybridization conditions, immobilized on the solid support, and washed prior to contacting with the synthesis primer (and polymerase). This modification will still result in the immobilization of two of the three primed nucleic acid template complexes (the complexes without a capture primer binding site will not bind the cognate binding partner on the support). Subsequent nucleic acid polymerization from the hybridized synthesis primer will release the desired asymmetrically-primed nucleic acid template complex.

Figure 4:
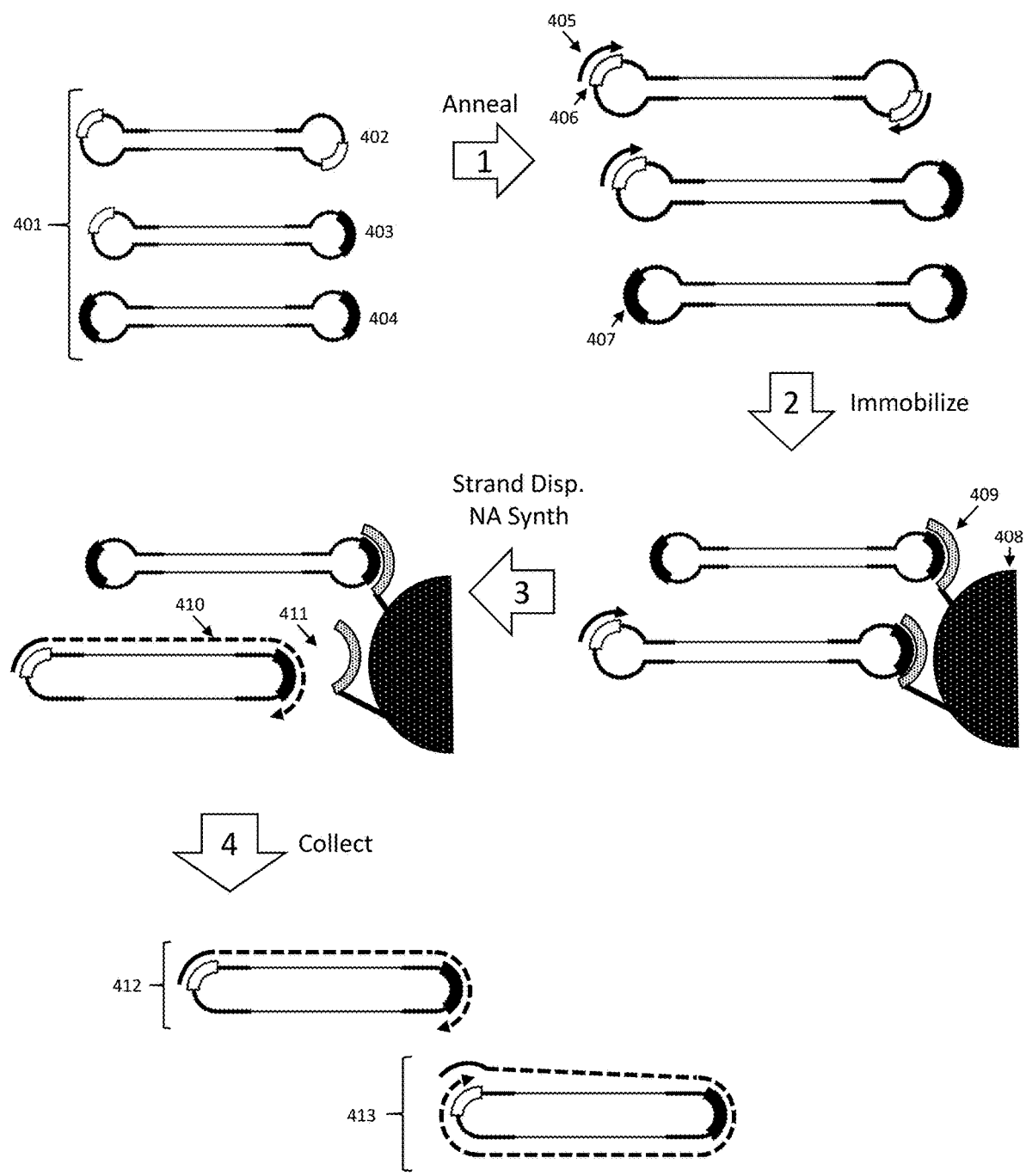
FIG. 4 illustrates an embodiment of a workflow for isolating asymmetrically-primed nucleic acids from a nucleic acid sample comprising a mixture of symmetrically-tagged and asymmetrically-tagged nucleic acid templates using strand displacement nucleic acid synthesis.

FIG. 4 shows an additional alternative workflow to that shown in FIG. 3. In FIG. 4, the nucleic acid sample (401) containing the three different adapter-tagged nucleic acid templates (two symmetrically tagged (402 and 404) and one asymmetrically tagged (403)) is contacted with synthesis primer (405) under suitable hybridization conditions, whereby the synthesis primer (405) anneals to primer binding site (406). These primer-hybridized complexes are then contacted directly to a solid support (408) onto which capture primer (409) has been immobilized, either covalently or non-covalently, resulting in the immobilization of nucleic acid templates containing capture primer binding site (407) to the solid support (i.e., through annealing of the capture primer binding site (407) and the capture primer (409)). Complexes that do not contain capture primer binding site (407) do not bind to the solid support and are removed, e.g., by washing. The bound nucleic acid template complexes are then subjected to a strand-displacing nucleic acid synthesis reaction (dotted line 410) whereby the asymmetrically-primed nucleic acid template complex is eluted from the capture primer (411), and thus the solid support. The eluted species (412) and (413), the latter in rolling-circle replication mode, may then be employed in any desired downstream process as desired by the user. It is noted that the contacting of the nucleic acid sample with the synthesis primer (405) and the solid support/capture primer (408/409) can occur in any suitable order or simultaneously. No limitation in this regard is intended.

It is again noted that asymmetrically-primed nucleic acid template complexes that have a region/nucleotide in the top strand of the insert that blocks nucleic acid synthesis before it reaches the hybridized capture primer will not be eluted, e.g., abasic regions, gaps, or other defects. This feature makes the eluted complexes particularly useful in subsequent sequence analysis (e.g., SMRT® Sequencing or nanopore-based sequencing), as certain damaged templates that will not provide high-quality sequencing data are removed from the pool (i.e., left on the solid support).

Figure 5:
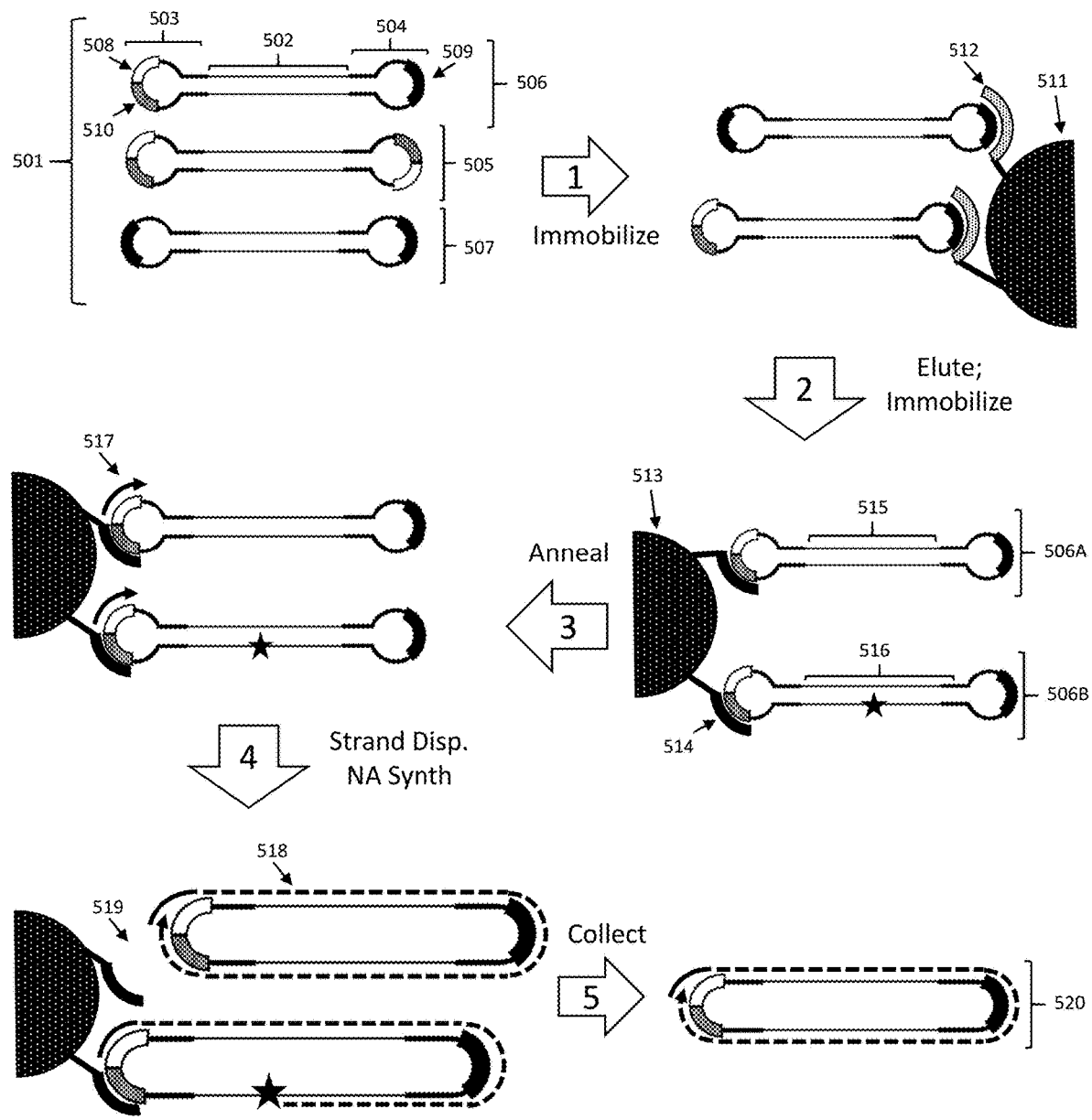
FIG. 5 illustrates an embodiment of a workflow for isolating asymmetrically-primed nucleic acids from a nucleic acid sample comprising a mixture of symmetrically-tagged and asymmetrically-tagged nucleic acid templates using strand displacement nucleic acid synthesis.

Another embodiment is shown in FIG. 5. The nucleic acid sample (501) is similar to the one shown in FIG. 3, including a mixture of nucleic acid templates comprising double-stranded nucleic acid inserts (502) and terminal adapters (503) and (504). As shown, sample (501) includes at three types of nucleic acid templates: two symmetrically-tagged nucleic acid templates (505 and 507), which include the same adapter at opposite template ends (adapter 503 in template 505 and adapter 504 in template 507), and one asymmetrically-tagged nucleic acid template (506), which includes different adapters at opposite template ends (503 at one end and 504 at the other). Similar to adapters (303) and (304) in FIG. 3, adapters (503) and (504) include a synthesis primer binding site (508) and a first capture primer binding site (509), respectively. In contrast to adapter (303) in FIG. 3, however, adapter (503) also includes a second capture primer binding site (510) that is different from the first capture primer binding site (i.e., second capture primer binding site (510) has a sequence sufficiently different from first capture primer binding site (509) such that it will hybridize to a different cognate capture primer under suitably stringent nucleic acid hybridization conditions). Second capture primer binding site (510) is positioned 3' of the synthesis primer binding site (508) in adapter (503).

In step 1, nucleic acid sample (501) is contacted to a first solid support (511) with an immobilized first capture primer (512) specific for the first capture primer binding site (509) under nucleic acid hybridization conditions. The first solid support can be any suitable material in any suitable form, including surface modified beads, resins, nanoparticles, or planar surfaces. The first capture primer can be immobilized in any suitable manner, covalently or non-covalently, that permits its hybridization to the first capture primer binding site (509) in adapter (504). Out of the three nucleic acid templates (505, 506, and 507), only the two with adapter (504), and thus first capture primer binding site (509), anneal to the first capture primer (templates 506 and 507). Nucleic acid template (505), which has only adapter (503), is removed from the mixture as supernatant (e.g., during a washing step).

After removing the non-binding nucleic acid templates from solid substrate (511), including nucleic acid template (505) (and any other nucleic acid without adapter 504), the bound templates are eluted from the first capture primer in step 2. In this step of the workflow, strand displacement synthesis is not used to elute the templates bound to the first capture primer. Rather, any other suitable method for elution can be used, e.g., by denaturing the annealed first capture primer from the first capture primer binding site (e.g., using chemical or physical means, e.g., heat denaturation, using a competitive capture primer, and the like) or by disruption of the link between the first capture primer and the solid support (511) (e.g., chemical cleavage, enzyme digestion, and the like). No limitation in this regard is intended. It is noted that the nucleic acid templates eluted from solid support (511) may be free of hybridized first capture primer (as shown in FIG. 5) or may still have it bound (not shown). This will not adversely affect the next steps of the workflow.

The templates eluted from the first solid support are then contacted with a second solid support (513) with an immobilized second capture primer (514) specific for the second capture primer binding site (510) under suitably stringent nucleic acid hybridization conditions. Out of the two DNA template species that bound to and were isolated from the first solid support (506 and 507), only the one with adapter (503) anneals to the second capture primer (i.e., nucleic acid template (506)). The remaining nucleic acid templates (507), which has only adapter (504), is removed from the mixture as supernatant (e.g., during a washing step). Thus, only asymmetrically-tagged species with adapter (503) on a first end and adapter (504) on the opposite end are bound to the second capture primer (514) on the second solid support (513). In FIG. 5, two different types of asymmetrically-tagged nucleic acid template (506) are shown. The first (506A) has a fully nucleic-acid-synthesis-competent insert (515) and the second (506B) has an insert (516) that is not fully nucleic-acid-synthesis-competent. In FIG. 5, insert (516) has a site in the bottom strand, indicated by a star, that stops nucleic acid synthesis. The site may be damage to the insert or may be the presence of a modification that blocks nucleic acid synthesis; no limitation in this regard is intended. In step 3, a synthesis primer (517) specific for the synthesis primer binding site (508) in adapter (503) is contacted to the solid support-bound templates under suitably stringent hybridization conditions to allow for annealing of the synthesis primer (517) to its cognate synthesis primer binding site (508). In step 4, the solid support-bound and synthesis-hybridized templates are contacted with a nucleic acid synthesis reagent mixture that supports nucleic acid synthesis by a strand-displacing polymerase from the hybridized synthesis primer. It is noted here that the synthesis primer can be hybridized to the templates at any suitable time prior to the nucleic acid synthesis reaction, e.g., prior to, during, or after binding to the first or second solid support (with the caveat that any treatment of the templates after synthesis primer hybridization does not prevent its ability to serve as an initiation site for nucleic acid synthesis). In certain embodiments, the polymerase is complexed with the synthesis primer prior to its hybridization to the synthesis primer binding site. In other embodiments, however, the polymerase is added at any suitable time after hybridization of the synthesis primer, e.g., before, during, or after contacting to the first or second solid support. Because of the orientation of the second capture primer binding site (510) and the synthesis primer binding site (508) (i.e., the second capture primer binding site (510) is at a location 3' of the synthesis primer binding site (508)), nucleic acid synthesis proceeds from the hybridized synthesis primer (517) in a direction away from the hybridized capture primer (514) and towards the template insert region (indicated by the dotted line 518). Therefore, in order to displace capture primer (514) hybridized to the second capture primer binding site from a nucleic acid template, the polymerase must proceed through the entire first strand of the insert region, around the adapter at the opposite end (i.e., adapter 504), and through the entire second strand of the insert region. Thus, if nucleic acid synthesis is blocked or terminated at any location before the polymerase reaches the second capture primer binding site (510), the template will remain bound to the solid support (via annealing to the second capture primer). As noted above, nucleic acid template (506A) has a fully nucleic-acid-synthesis-competent insert (515) and the nucleic acid template (506B) has an insert (516) that is not fully nucleic-acid-synthesis-competent. As such, nucleic acid template (506A) is eluted from the capture primer by the activity of the nucleic acid polymerase (519) while nucleic acid template (506B) is not due to the presence of a site that blocks nucleic acid polymerization (indicated by the star). Therefore, eluted nucleic acid templates are not only asymmetrically-primed, but are also fully nucleic acid synthesis competent, which makes it suitable for any desired downstream processes or analyses, especially when used for subsequent sequence analyses (e.g., SMRT® Sequencing and nanopore-based sequencing). In step 5, the eluted templates (520) are collected from the supernatant of the solid support. The polymerization reaction can be stopped at any time after elution/collection or allowed to continue, as desired by a user.

In certain embodiments, the isolated asymmetrically-primed nucleic acid templates can be subjected to additional enrichment/isolation processes, e.g., processing to isolate nucleic acid templates comprising one or more regions of interest in the insert region of the template.

Figure 6:
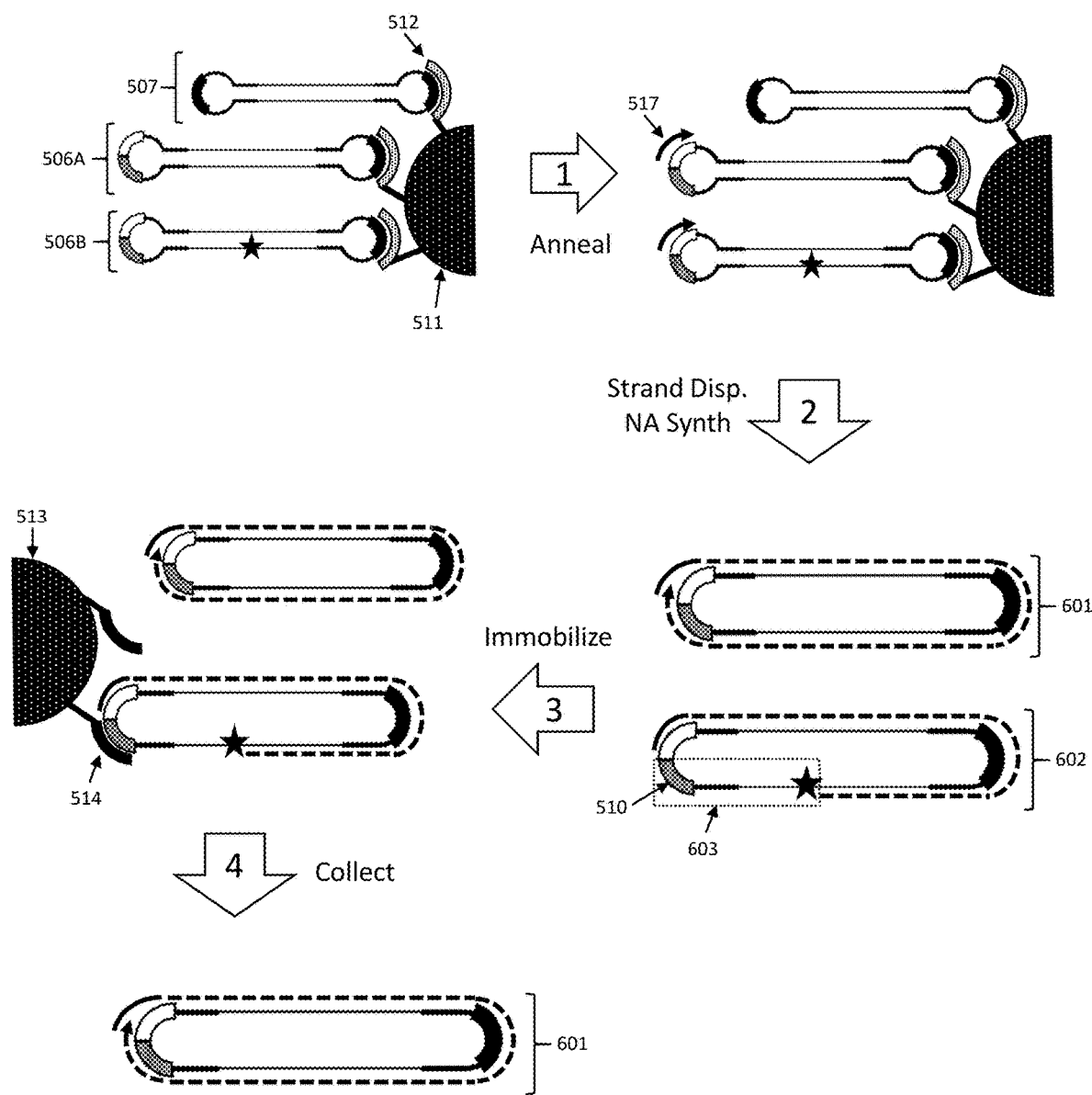
FIG. 6 illustrates an embodiment of a workflow for isolating asymmetrically-primed nucleic acids from a nucleic acid sample comprising a mixture of symmetrically-tagged and asymmetrically-tagged nucleic acid templates using strand displacement nucleic acid synthesis.
Figure 7:
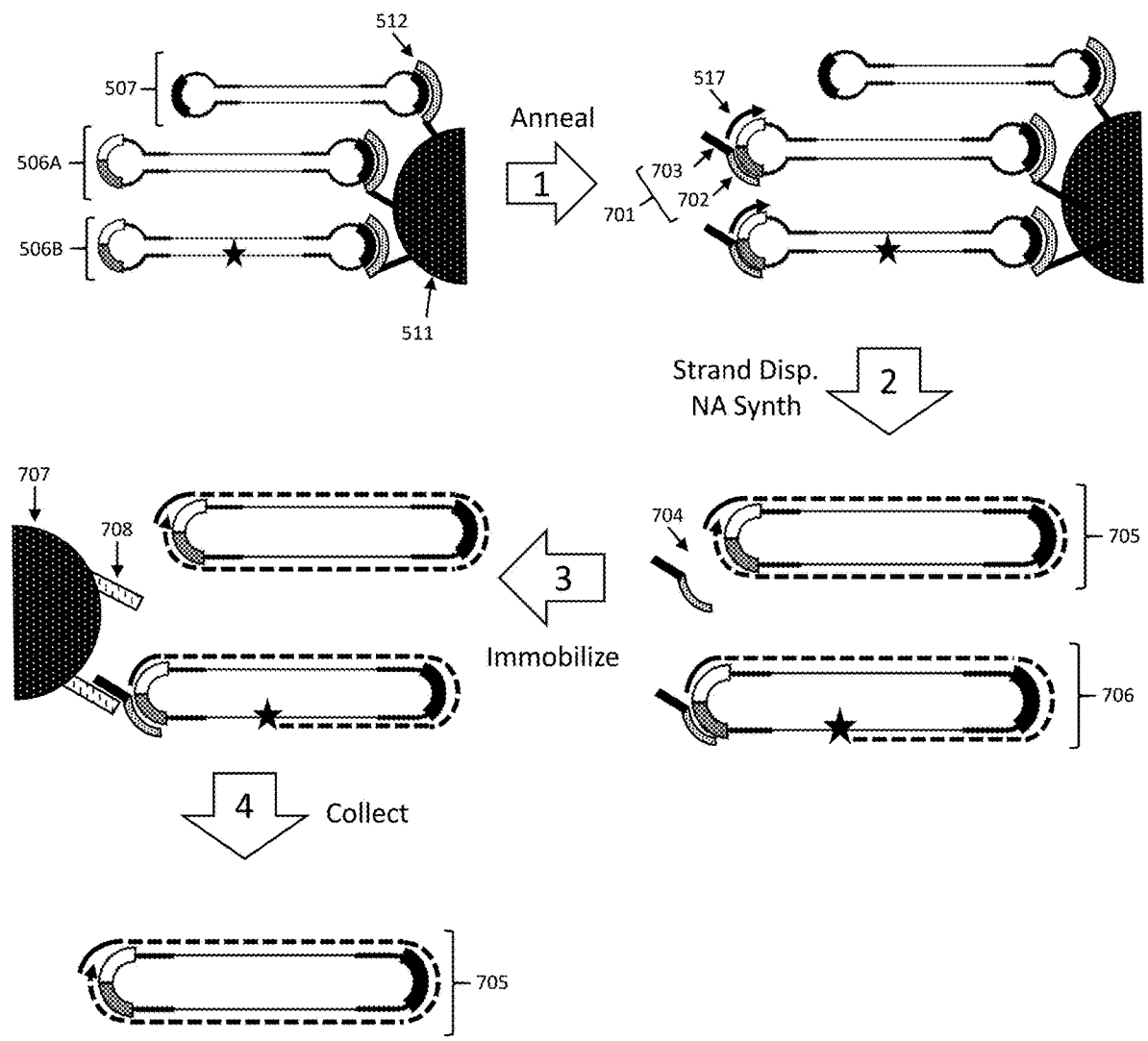
FIG. 7 illustrates an embodiment of a workflow for isolating asymmetrically-primed nucleic acids from a nucleic acid sample comprising a mixture of symmetrically-tagged and asymmetrically-tagged nucleic acid templates using strand displacement nucleic acid synthesis.

FIGS. 6 and 7 show variations of the workflow described in FIG. 5. In FIG. 6, the templates are shown immobilized on the first solid support (511) through hybridization to capture primer 1 (512) as was done in FIG. 5 (the template with the polymerase blocking site (506B) is shown in FIG. 6, but was not shown in the first immobilization step in FIG. 5). Unlike in FIG. 5, the nucleic acid templates immobilized to the substrate through capture primer 1 are contacted with synthesis primer (517) and subjected to a nucleic acid synthesis reaction with a strand displacing polymerase to elute nucleic acid templates that include adapter (503). The polymerization reaction is allowed to proceed after elution which allows fully nucleic-acid-synthesis-competent and asymmetrically-primed nucleic acid templates (506A) to go into rolling circle replication (601) while asymmetrically-primed nucleic acid templates with a polymerization blocking site (506B) do not (602). These latter templates thus have a single-stranded region (in box 603) that includes the second capture primer binding site (510). Thus, when this eluted mixture of asymmetrically-primed nucleic acid templates is contacted to the second solid substrate (513) with immobilized second capture primer (514) under suitably stringent nucleic acid hybridization conditions (step 3), only the non-fully-synthesis-competent templates will be immobilized, i.e., through hybridization to capture primer (514). Collection of the non-binding templates in step 4 will thus result in isolation of asymmetrically-primed nucleic acid templates that are fully synthesis competent (601).

In FIG. 7, the templates are again shown immobilized on the first solid support (511) as was done in FIG. 5 (the template with the polymerase blocking site (506B) is shown in FIG. 7, but was not shown in the first immobilization step in FIG. 5). Unlike in FIG. 5, in step 1 of FIG. 7, the immobilized nucleic acid templates are contacted under suitably stringent hybridization conditions with synthesis primer (517) and second capture primer (701) that comprises a capture primer domain (702) that is specific for capture primer binding site (510) and a capture moiety (703) that is a first member of a binding pair. Capture primer (701) is not capable of initiating nucleic acid synthesis as is synthesis primer (517). Any suitable way to render capture primer (701) synthesis-incompetent may be used (e.g., a 3' terminal dideoxynucleotide, a 3' non-hybridizing nucleotide/nucleotide sequence, etc.). In step 2, the primed and immobilized complexes are subjected to a nucleic acid synthesis reaction with a strand displacing polymerase to elute nucleic acid templates that include adapter (503). The polymerization reaction is allowed to proceed after elution which allows the polymerase on fully nucleic-acid-synthesis-competent and asymmetrically-primed nucleic acid templates to displace the second capture primer (704) and go into rolling circle replication (template 705) while the polymerization reaction on asymmetrically-primed nucleic acid templates with a polymerization blocking site do not displace the second capture primer (template 706). In step 3, the eluted mixture of asymmetrically-primed nucleic acid templates (i.e., 705 and 706) is contacted to a second solid substrate (707) with immobilized binding partners (708) for the capture moiety on the second capture primer under suitable binding conditions between capture moiety (703) and its cognate binding partner (708). Only the non-fully-synthesis-competent templates (706) will be immobilized to the solid support through binding of the capture moiety (703) of the capture primer (701) to its cognate binding partner (708) on solid substrate (707). Fully synthesis-competent templates (705) do not bind to the binding partner (708) because the capture primer has been eluted from the template. Collection of the non-binding templates in step 4 will thus result in isolation of asymmetrically-primed nucleic acid templates that are fully synthesis competent (705) from those that are not (706).

Figure 8:
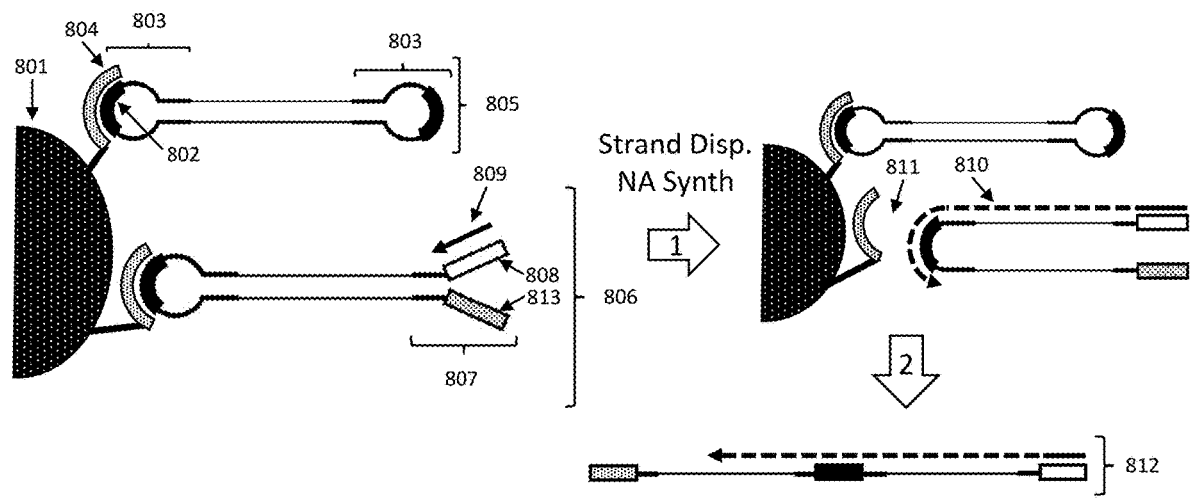
FIG. 8 illustrates an embodiment of a workflow for isolating asymmetrically-primed nucleic acids from a nucleic acid sample comprising a mixture of symmetrically-tagged and asymmetrically-tagged nucleic acid templates using strand displacement nucleic acid synthesis in which one of the adapters is a hairpin adapter and the other is a Y-adapter.

While the previous embodiments were drawn to isolation of asymmetrically primed nucleic acid templates with hairpin adapters at both ends, in certain embodiments, asymmetrically primed nucleic acids having a non-hairpin adapter at one end and a hairpin adapter at the other are isolated. One example of such a workflow is shown in FIG. 8. In this figure, templates from a mixed sample of symmetrically-tagged and asymmetrically-tagged nucleic acids are immobilized to solid support (801) through hybridization of capture primer binding site (802) in adapter (803) to capture primer (804). Template (805) is symmetrically tagged with adapters (803) while template (806) is asymmetrically tagged with hairpin adapter (803) at a first end and Y-adapter (807) at the second (opposite) end. Y-adapter (807) includes a single stranded synthesis primer binding site (808) with an annealed synthesis primer (809) (symmetric templates with adapter 807 at both ends do not bind to capture primer (804) and thus are not shown). In step 1, strand displacing nucleic acid synthesis (dotted line 810) is initiated on the immobilized templates. Asymmetrically primed nucleic acid templates having adapter (807) at one end will be eluted (811) by the activity of the strand-displacing polymerase once it reaches the capture primer (804) annealed at capture primer binding site (802) in adapter (803) at the opposite end. Symmetric templates (805), which do not have synthesis primer binding site (808) will remain immobilized on the substrate via hybridization to the capture primer. The resulting eluted asymmetrically-primed nucleic acid template (812) can be collected (step 2) and employed in any desired downstream processes/analyses, including single molecule sequencing reactions (e.g., SMRT® Sequencing or nanopore-based sequencing). In an alternative embodiment (not shown), templates can be eluted from substrate (801) by non-strand-displacing polymerase methods, immobilized on a second substrate displaying capture primers for the other domain in the Y-adapter (813), and eluted by strand displacement nucleic acid synthesis to generate fully synthesis competent templates that are asymmetrically primed (this similar to the workflow in FIG. 5, except that the resulting isolated asymmetrically-tagged nucleic acid template is a linear double-stranded nucleic acid).

V. KITS AND SYSTEMS

The present disclosure also provides applied embodiments of the methods and compositions disclosed herein.

For example, in certain embodiments, the present disclosure provides kits that are used in preparation of the asymmetrically-primed nucleic acid constructs described herein. In some embodiments, a kit according to aspects of the present disclosure provides the materials for isolation of the asymmetrically-primed nucleic acid templates in accordance with the invention, as described elsewhere herein. As such, a kit will typically include those materials that are required to isolate asymmetrically-primed nucleic acid templates from a sample as described herein, e.g., in accordance with the various processes outlined above. As will be appreciated, depending upon the nature of the nucleic acid templates in the initial nucleic acid sample and the method used, the kit contents can vary. In certain embodiments, the kit can include one or more solid substrates comprising capture primers/capture moieties attached thereto (e.g., two sets of beads, one with a first capture primer/moiety and a second with a second capture/moiety conjugated thereto), a strand displacing nucleic acid polymerase (as described in detail herein), reagents for binding nucleic acid templates to the capture primers/moieties on the solid substrates, and reagents for performing a strand-displacing nucleic acid synthesis reaction. Reagents thus include, but are not limited to, hybridization/binding buffers, nucleic acid synthesis buffers, nucleotides, nucleic acid synthesis primers, capture primers, etc.

In some embodiments, kits further include reagents for generating tagged nucleic acid templates from a nucleic acid sample. For example, kits can include one or more types of hairpin adapters to generate symmetrically-tagged and/or asymmetrically-tagged nucleic acid templates. In some embodiments, such kits may also include appropriate ligation enzymes and protocols for attaching such adapters to the ends of double stranded nucleic acids, as well as any processing enzymes that may be desirable for treating the ends of the double stranded segments prior to ligation, e.g., phosphatases, exonucleases, and the like.

As certain capture primer/moiety binding and nucleic acid synthesis steps may be performed under different reaction conditions, separate buffers/reagents can be provided for each. Alternatively, a single set of buffers/reagents compatible for use in multiple steps of a workflow may be provided.

In addition, kits may include reagents for removing undesired nucleic acids or buffer components in a sample, including exonucleases, nucleic acid purification columns or beads, size-selection columns or spin tubes, affinity/capture reagents (e.g., biotin, avidin, capture primers, etc.). Further, kits may include reagents for generating the initial nucleic acid fragments to be tagged, including nucleic acid isolation reagents, fragmentation reagents (e.g., fragmentation columns, restriction enzymes, etc.).

In additional embodiments, a kit of the present disclosure may provide materials and methods not just for the isolation of asymmetrically-primed nucleic acid templates, but also for the use of such asymmetrically-primed nucleic acids in performing sequence analysis on such templates. Thus, in addition to the components set forth above, such kits may additionally include reagents used in such sequencing processes. For example, kits can include substrates that provide for optical confinement of nucleic acid synthesis complexes. In certain aspects, such substrates will typically include one or more arrays of zero mode waveguides (ZMW). Such waveguide arrays may further include surface treatments that provide for enhanced localization of synthesis complexes within the illumination volumes of such zero mode waveguides, e.g., as described in U.S. Pat. No. 8,975,216 (titled "Articles having localized molecules disposed thereon and methods of producing same"), hereby incorporated by reference herein in its entirety for all purposes. Additionally, such kits may optionally include nucleotide compositions for use in sequencing applications, including, for example labeled nucleotides that include fluorescent or otherwise detectable labeling groups coupled to the phosphate groups in a nucleoside polyphosphate construct at a phosphate group other than the alpha phosphate. A variety of other types of labeled and unlabeled nucleotides may be optionally includes within the kits and are generally known in the art. In addition, reagents that find use in nanopore-based sequencing can be included in kits of the present disclosure, including nanopore-bearing substrates, reagents for preparing templates for nanopore sequence analysis, e.g., adapters and/or molecular motors for guiding nucleic acids through/over a nanopore (e.g., helicases, polymerases, etc.), nucleotide analogs comprising nanopore-detectable labels, and the like.

VI. UTILITY

The methods and compositions of the present disclosure provide advantages over current nucleic acid template preparation/isolation methods.

For example, asymmetrically-primed nucleic acid templates are expected to have improved loading characteristics in zero-mode waveguides (ZMW) employed in SMRT® Sequencing (or other nanometer-scale well structures) as compared to symmetrically-primed templates due to steric considerations. For example, symmetrically-primed templates have two active polymerases bound, leading to less efficient loading. In addition, if such complexes do load, having two polymerases in a single ZMW leads to shorter reads and/or noisy data, as both polymerases will be working on the same substrate at the same time in the same ZMW.

In addition, asymmetrically-tagged nucleic acid templates isolated according to aspects of the present disclosure (i.e., using strand-displacing nucleic acid synthesis to elute from a capture primer) have improved quality, as they have been screened to be nucleic acid synthesis-competent, in some embodiments being fully nucleic acid synthesis competent. In other words, nucleic acid templates that have blockages to nucleic acid synthesis (e.g., damaged templates) are removed from the pool of templates. The improved quality increases their usefulness in a number of downstream assays, including but not limited to nucleic acid sequence analysis.

VII. EXAMPLES

Example 1

A. Generating Asymmetrically-Primed Templates from Symmetrically-Tagged Nucleic Acids Symmetrically-tagged nucleic acid templates were made as follows:

10 µg of PBR322 plasmid was linearized with HindIII enzyme followed by ExoVII treatment to form blunt-end 4.3 kb dsDNA. Identical hairpin-adaptors containing a primer binding site were ligated to the linear dsDNA to form a nucleic acid sample containing templates with the same hairpin adapter at both ends, i.e., symmetrically-tagged nucleic acid templates. The symmetrically-tagged nucleic acid templates were purified using AMPure beads (Beckman Coulter Life Sciences (Agencourt); Indianapolis, Ind.) according to manufacturer's instructions conditions and quantitated with a Qubit Fluorometer (Thermo Fisher Scientific; Waltham, Mass.).

The symmetrically-tagged nucleic acid templates were contacted under suitable hybridization conditions (80° C. heat denaturing for 2 minutes, followed by 30-60 minutes of incubation at 37° C.) with either: (i) a nucleic acid synthesis primer specific for the primer binding site in the hairpin adapter, or (ii) a 1:1 mixture of the same nucleic acid synthesis primer and a capture primer that has (a) a capture region and (b) a primer region that is specific for the primer binding site in the hairpin adapter. Unlike the synthesis primer, the capture primer is not competent to serve as an initiation site for nucleic acid synthesis because the capture region, which does not hybridize to the template, is located 3' to the primer domain. The final concentration of total primer in each sample was 100 nM and the template was at a concentration of 10 nM. After hybridization, each sample was split into two. To one of these two samples, a Φ29 polymerase was added and incubated at 30° C. for 4 hours and then placed under nucleic acid synthesis conditions (30 mM MgAc2 and 50 μM of deoxynucleosides (dNTPs)) for 30 minutes.

Figure 9:
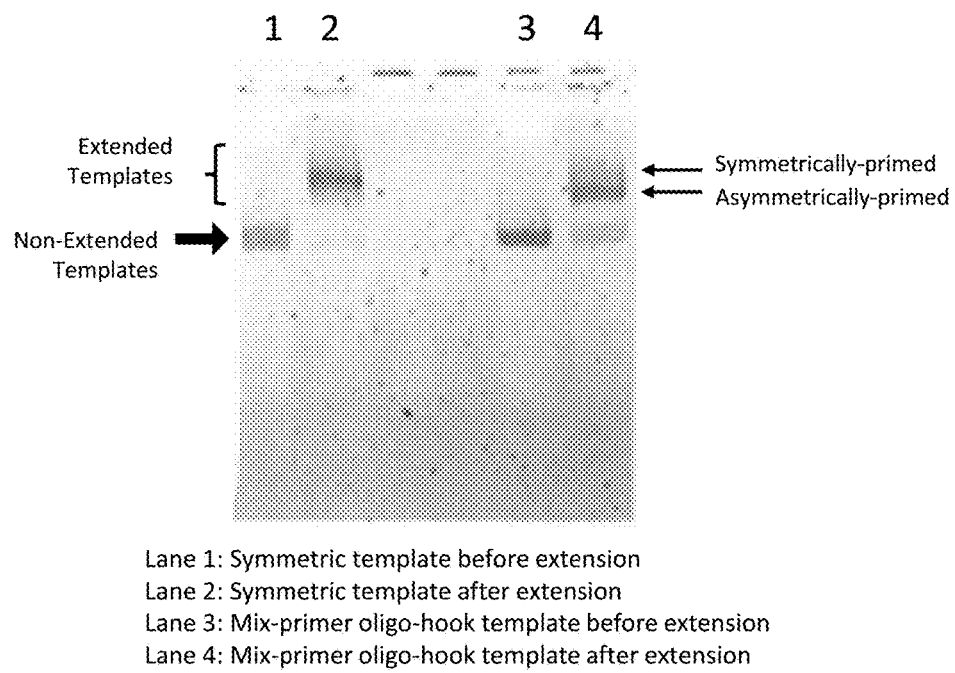
FIG. 9 shows agarose gel analysis of symmetrically-tagged nucleic acid templates treated as follows (as described in Example 1): nucleic acid templates primed with only a synthesis primer and in the absence of nucleic acid synthesis (lane 1); nucleic acid templates primed with only a synthesis primer and after nucleic acid synthesis (lane 2); nucleic acid templates primed with a 1:1 mixture of a synthesis primer and a capture primer in the absence of nucleic acid synthesis (lane 3); and nucleic acid templates primed with a 1:1 mixture of a synthesis primer and a capture primer after nucleic acid synthesis (lane 4). Bands corresponding to extended and non-extended templates are indicated.

FIG. 9 shows the agarose gel analysis of the four samples. Lane 1 shows the nucleic acid species in the sample primed with only the synthesis primer and in the absence of nucleic acid synthesis; lane 2 shows the nucleic acid species in the sample primed with only the synthesis primer and after nucleic acid synthesis; lane 3 shows the nucleic acid species in the sample primed with the 1:1 mixture of the synthesis primer and the capture primer in the absence of nucleic acid synthesis; and lane 4 shows the nucleic acid species in the sample primed with the 1:1 mixture of the synthesis primer and the capture primer after nucleic acid synthesis.

The lower band in the gel in FIG. 9 is the size of the templates in the absence of nucleic acid synthesis (the only band in lanes 1 and 3; indicated as non-extended templates (arrow)). Upon nucleic acid synthesis, nearly all of the templates primed with only the synthesis primer (lane 2) were capable of nucleic acid synthesis (indicated as extended templates (bracket)). In contrast, a significant number of the templates primed with the 1:1 mixture of synthesis primer and capture primer remained non-extended (lane 4). These templates represent those to which capture primers have hybridized to the primer binding sites in both of the terminal hairpin adapters and thus cannot support nucleic acid synthesis (i.e., no synthesis primer is hybridized). In addition, the extended templates segregated into two species: a larger species that represents templates with two synthesis primers hybridized (indicated as symmetrically-primed) and thus that can extend from both ends simultaneously, and a smaller species having a synthesis primer ate one end and a capture primer at the other (indicated as asymmetrically-primed) and thus can extend from only one end of the template. (Note that virtually all of the extended species in lane 2 are the larger species, i.e., the symmetrically-primed extended template species.)

This experiment verifies the competitive binding characteristics of the synthesis primer and capture primer for identical primer binding sites and indicates that asymmetrically-primed templates can be produced from symmetrically-tagged nucleic acid templates (these are present in the extended templates in lane 4; the smaller species).

B. Sequence Analysis of Symmetrically-Tagged Nucleic Acid Templates that are Symmetrically- or Asymmetrically-Primed Symmetrically- or asymmetrically-primed nucleic acid templates were generated as above and subjected to Single Molecule, Real-Time (SMRT®) Sequencing analysis (Pacific Biosciences of California, Inc.; Menlo Park, Calif.).

Figure 10:
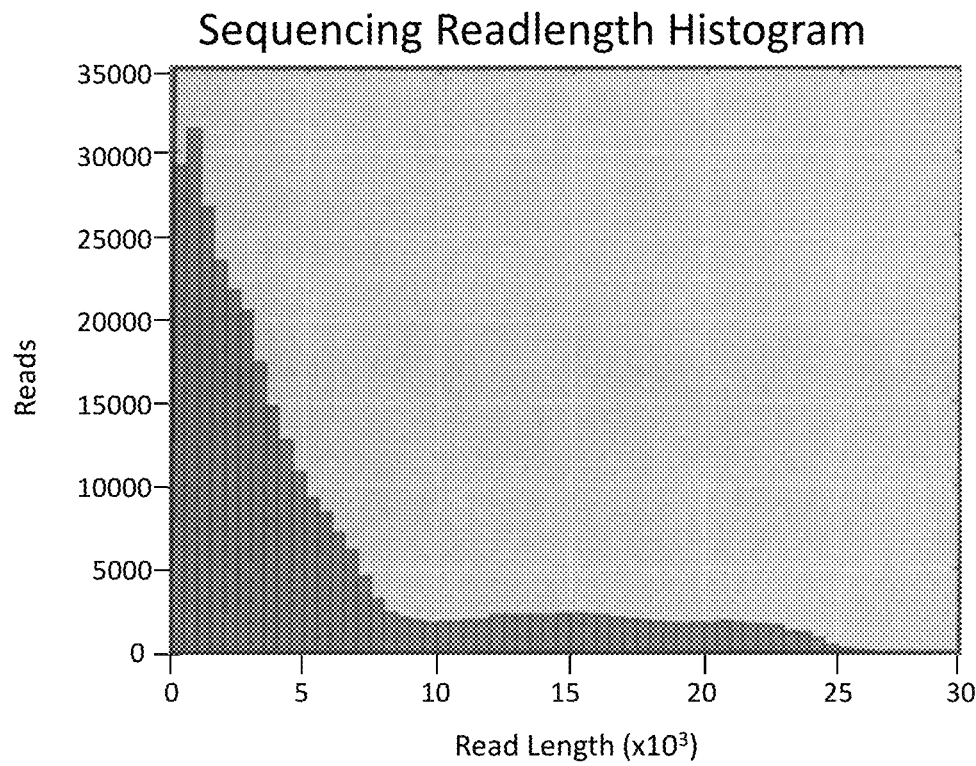
FIG. 10 shows SMRT® Sequencing results from symmetrically-tagged nucleic acid templates that are symmetrically-primed.
Figure 11:
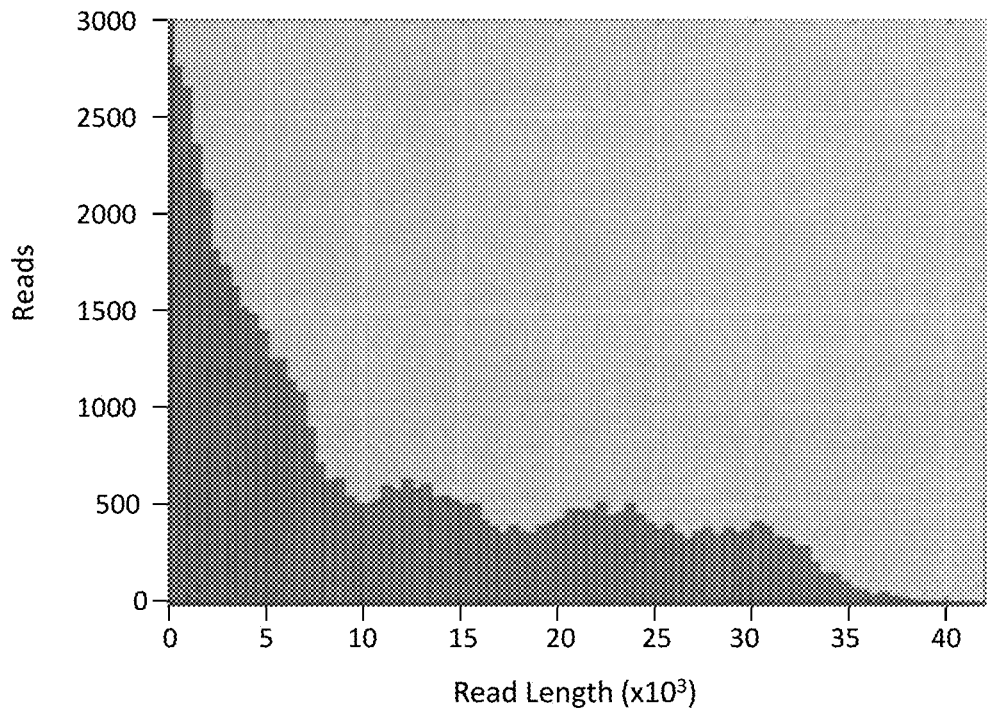
FIG. 11 shows SMRT® Sequencing results from symmetrically-tagged nucleic acid templates that are asymmetrically-primed.

FIG. 10 shows SMRT® Sequencing results from symmetrically-primed nucleic acid templates while FIG. 11 shows SMRT® Sequencing results from asymmetrically-primed nucleic acid templates isolated using a capture primer. As is clear from these Figures, the isolated, asymmetrically-primed nucleic acid templates provided improvements in many key aspects of the analysis over the symmetrically-primed nucleic acid templates. For example, the average number of contiguous bases incorporated into a nascent strand during template-directed synthesis in the SMRT® Sequencing reaction (the "Polymerase Read Length Mean") for the symmetrically-primed templates was 5,373 bases while this value for the asymmetrically-primed templates reached 11,089 bases (a greater than 2-fold improvement). Similarly, the value for both the 95% read length and the maximum read length were also improved in the asymmetrically-primed templates versus the symmetrically-primed templates (see the "Polymerase Read Length 95%" and "Polymerase Read Length Max" values). Moreover, the distribution of the read lengths was improved in the asymmetrically-primed templates versus the symmetrically-primed templates (see the histograms on the bottom of FIGS. 10 and 11). For example, the symmetrically-primed templates have a higher fraction of terminations in the 1,000 bases to 8,000 bases range than the asymmetrically-primed templates.

Example 2

Asymmetrically-tagged DNA templates were generated using the SMRTBELL® Asymmetric Auxiliary Template Prep Kit (Pacific Biosciences; Menlo Park, Calif.) according to manufacturer's instructions. 10 fmol of this asymmetric template DNA was annealed to 1:1 mixture of sequencing primer and capture oligonucleotide with 3'-$A_{(18)}$ tail. The annealed sample was contacted with DNA polymerase according to manufacturer's instructions.

The resulting template/DNA complex was treated with 150 μL of poly(T) magnetic beads (Magbead Binding Kit; Pacific Biosciences; Menlo Park, Calif.) for 30 minutes in 1×MOPS buffer with 400 mM KCl. The supernatant was removed and the bead-bound complex was incubated in extension buffer (100 μM dNTPs, 30 mM MgCl₂, 120 mM KAc, and 40 mM DTT) for 90 minutes. The supernatant of the extension reaction was collected and purified with AMPure beads (Sample Prep Kit; Pacific Biosciences; Menlo Park, Calif.) without the ethanol wash. The extension product was eluted in 30 μL 1×MOPS buffer with 50 mM KAC and 0.2 mM SrAc₂. The resulting complex was quantitated with a Qubit Fluorometer (Thermo Fisher Scientific, Waltham, Mass.).

The purified complex was then sequenced by SMRT® Sequencing on a SEQUEL® System (Pacific Biosciences; Menlo Park, Calif.) with two methods:

1. Magbead loading method: the complex was bound to Magbeads and loaded to the sample plate according to the Magbead loading standard operation protocol (Pacific Biosciences; Menlo Park, Calif.);

2. Diffusion loading method: the complex was diluted to 80 μL with Magbead binding buffer (Pacific Biosciences; Menlo Park, Calif.) and the resulting solution was loaded onto the sample plate according to diffusion loading standard operation protocol (Pacific Biosciences; Menlo Park, Calif.).

Figure 12:
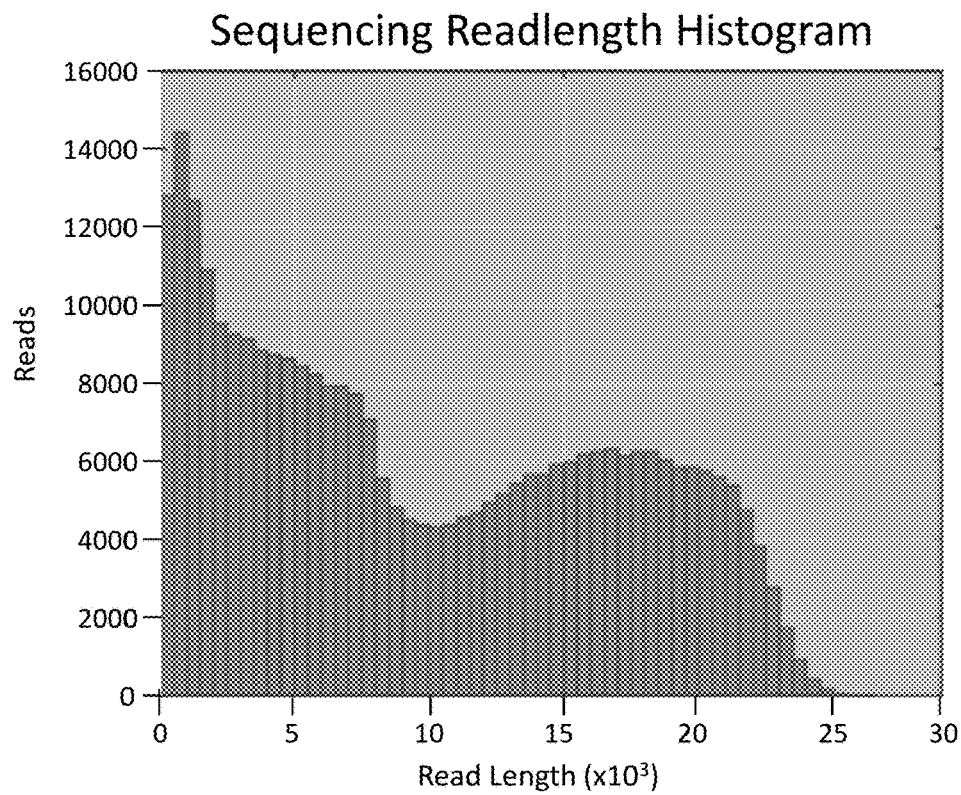
FIG. 12 shows SMRT® Sequencing results from asymmetrically-tagged, primed, and isolated nucleic acid templates using MagBead loading.
Figure 13:
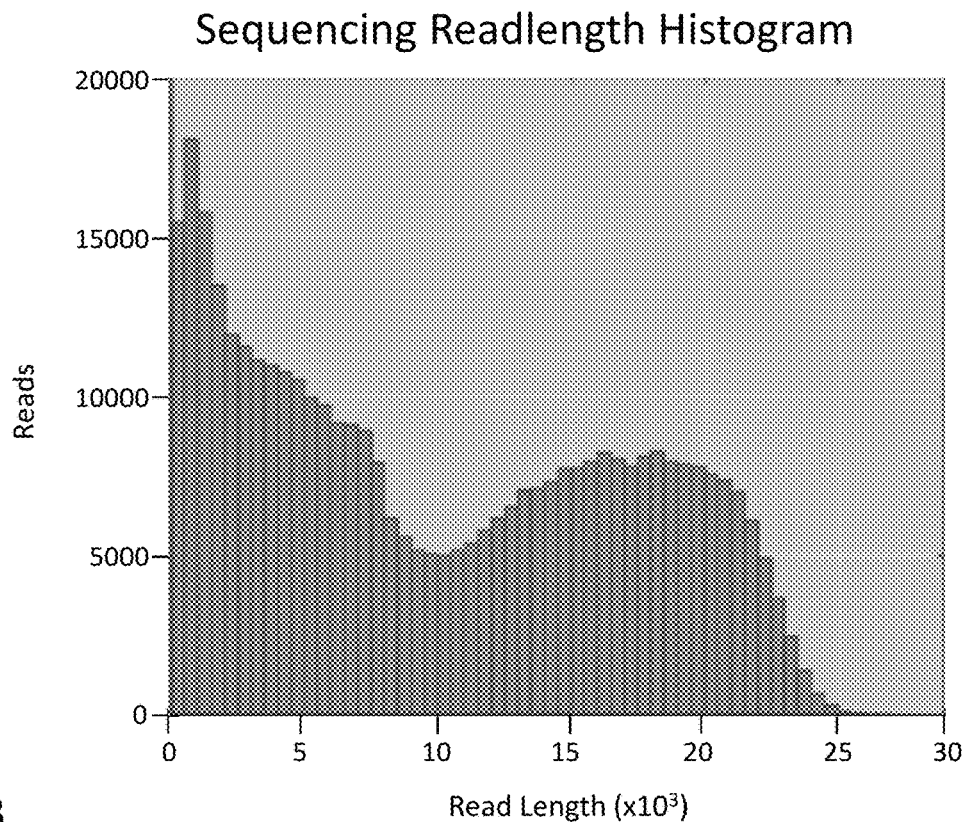
FIG. 13 shows SMRT® Sequencing results from asymmetrically-tagged, primed, and isolated nucleic acid templates using Diffusion loading.

Both methods gave similar sequencing results. Specifically, as shown in FIG. 12 (MagBead loading) and FIG. 13 (Diffusion loading), the number of aligned sequencing reads were above 300,000 and the readlength was about 10,000 (for a 4-hour movie). The improvement in readlength in these asymmetrically-tagged and primed samples is similar to that observed for asymmetrically-primed templates over symmetrically-primed templates as shown in Example 1 (see FIGS. 10 and 11, described above).

Although described in some detail for purposes of illustration, it will be readily appreciated that a number of variations known or appreciated by those of skill in the art may be practiced within the scope of present invention. To the extent not already expressly incorporated herein, all published references and patent documents referred to in this disclosure are incorporated herein by reference in their entirety for all purposes.

What is claimed is:

1. A method for isolating nucleic acid synthesis-competent nucleic acid templates comprising:
    obtaining a sample comprising asymmetrically tagged nucleic acid templates each comprising a double-stranded insert region, a first hairpin adapter at one end, and a second hairpin adapter at the opposite end, wherein the first hairpin adapter comprises a synthesis primer binding site and a capture primer binding site positioned 3' of the synthesis primer binding site;
    contacting the nucleic acid sample with a capture primer specific for the capture primer binding site under nucleic acid hybridization conditions;
    immobilizing capture primer-hybridized nucleic acid templates to a solid support via a capture region on the capture primer;
    contacting the nucleic acid templates immobilized to the solid support with a nucleic acid polymerase having strand displacement activity under conditions that promote nucleic acid synthesis from a synthesis primer hybridized to the synthesis primer binding site; and
    collecting nucleic acid templates eluted from the solid support by the strand displacement activity of the nucleic acid polymerase, thereby isolating nucleic acid synthesis-competent nucleic acid templates.

2. The method of claim 1, wherein the synthesis primer is contacted to the sample with the capture primer in the first contacting step.

3. The method of claim 1, wherein the synthesis primer is contacted to the sample under nucleic acid hybridization conditions after the immobilizing step.

4. The method of claim 1, wherein the capture primer is covalently bound to the solid support via the capture region.

5. The method of claim 1, wherein the capture primer is non-covalently bound to the solid support via the capture region.

6. The method of claim 5, wherein the solid support comprises a binding partner for the capture region on the capture primer.

7. The method of claim 6, wherein the binding partner is selected from the group consisting of: a nucleotide sequence, an antigen, an antibody or a binding fragment thereof, avidin, streptavidin, and biotin.

8. The method of claim 1, wherein the sample further comprises symmetrically tagged nucleic acid templates each comprising either the first hairpin adapter at both ends or the second hairpin adapter at both ends, wherein the second hairpin adapter comprises a second capture primer binding site, and wherein before the first contacting step, the method further comprises:
    contacting the nucleic acid sample with a second capture primer specific for the second capture primer binding site under nucleic acid hybridization conditions;
    immobilizing second capture primer-hybridized nucleic acid templates to a second solid support via a capture region on the second capture primer; and
    eluting and collecting the nucleic acid templates bound to the second solid support.

9. The method of claim 8, wherein the second capture primer is covalently bound to the second solid support via the capture region on the second capture primer.

10. The method of claim 8, wherein the second capture primer is non-covalently bound to the second solid support via the capture region on the second capture primer.

11. The method of claim 10, wherein the second solid support comprises a binding partner for the capture region on the second capture primer.

12. The method of claim 11, wherein the binding partner is selected from the group consisting of: a nucleotide sequence, an antigen, an antibody or a binding fragment thereof, avidin, streptavidin, and biotin.

13. The method of claim 8, wherein eluting from the second solid support is not achieved by strand displacement nucleic acid synthesis.

14. The method of claim 1, wherein the strand displacing polymerase is a Φ29 DNA polymerase, a homolog of a Φ29 DNA polymerase, a modified version of a Φ29 DNA polymerase, or a modified version of a homolog of a Φ29 DNA polymerase.

15. The method of claim 1, wherein the isolated nucleic acid templates are subjected to sequence analysis.

16. The method of claim 15, wherein the sequence analysis comprises a sequencing-by-synthesis sequencing reaction.

17. The method of claim 16, wherein the nucleic acid polymerase remains associated with the template nucleic acids after elution and is used in the sequencing-by-synthesis sequencing reaction.

18. The method of claim 17, wherein the sequencing-by-synthesis sequencing reaction is a single molecule, real-time sequencing-by-synthesis sequencing reaction.

19. The method of claim 15, wherein the sequence analysis comprises a nanopore sequencing reaction.

* * * * *